US011918646B2

(12) United States Patent
Cui et al.

(10) Patent No.: US 11,918,646 B2
(45) Date of Patent: Mar. 5, 2024

(54) DRY ADJUVANTED IMMUNE STIMULATING COMPOSITIONS AND USE THEREOF FOR MUCOSAL ADMINISTRATION

(71) Applicant: Board of Regents, The University of Texas System, Austin, TX (US)

(72) Inventors: Zhengrong Cui, Austin, TX (US); Sachin G. Thakkar, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/771,648

(22) PCT Filed: Dec. 11, 2018

(86) PCT No.: PCT/US2018/064837
§ 371 (c)(1),
(2) Date: Jun. 10, 2020

(87) PCT Pub. No.: WO2019/118393
PCT Pub. Date: Jun. 20, 2019

(65) Prior Publication Data
US 2021/0170019 A1    Jun. 10, 2021

Related U.S. Application Data

(60) Provisional application No. 62/597,037, filed on Dec. 11, 2017.

(51) Int. Cl.
*A61K 39/39*       (2006.01)
*A61K 39/02*       (2006.01)
(Continued)

(52) U.S. Cl.
CPC .............. *A61K 39/39* (2013.01); *A61K 39/02* (2013.01); *A61K 39/12* (2013.01); *A61K 2039/543* (2013.01); *A61K 2039/55505* (2013.01)

(58) Field of Classification Search
None
See application file for complete search history.

(56) References Cited

U.S. PATENT DOCUMENTS 4,534,343 A * 8/1985 Nowacki ........... A61M 15/0086
128/200.23
5,714,374 A    2/1998 Arnold et al.
(Continued)

FOREIGN PATENT DOCUMENTS

EP         1905449       4/2008
WO    WO 2003/090715    11/2003
(Continued)

OTHER PUBLICATIONS

Isaka et al. (Index of Nagoya Med J. 2001; 45(1): 5-15).*
(Continued)

*Primary Examiner* — Shanon A. Foley
(74) *Attorney, Agent, or Firm* — Parker Highlander PLLC

(57) ABSTRACT

Described herein are dry immunogenic compositions and methods of freezing aluminum-containing vaccines such that when converted into a dried powder, the dry composition can be readily administered without loss of activity. Also described are methods of intranasal administering dry immunogenic compositions comprising antigens and aluminum adjuvants.

11 Claims, 8 Drawing Sheets

Figure 1A:
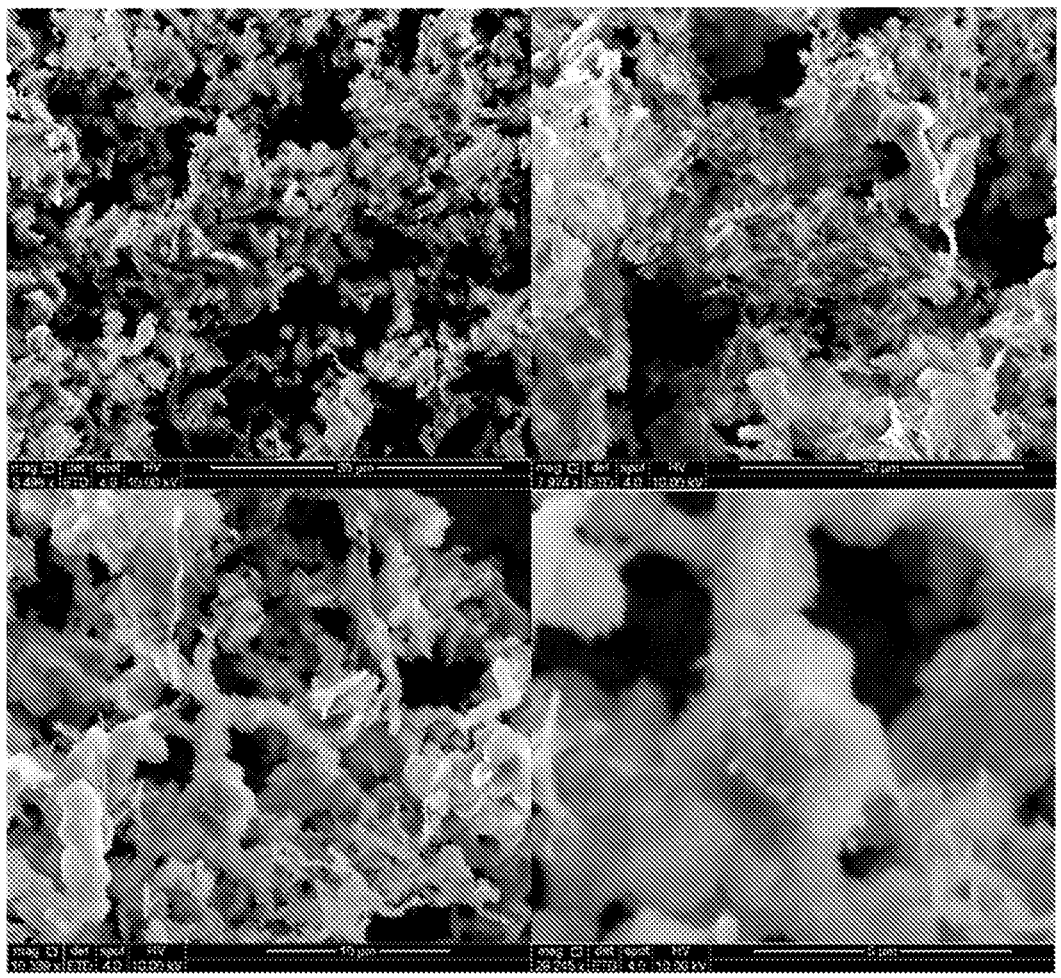

(51) Int. Cl.
*A61K 39/12* (2006.01)
*A61K 39/00* (2006.01)

(56) References Cited

U.S. PATENT DOCUMENTS

| | | | |
|---|---|---|---|
| 6,284,282 B1 | 9/2001 | Maa et al. | |
| 6,585,957 B1 | 7/2003 | Adjei et al. | |
| 6,630,169 B1* | 10/2003 | Bot | A61K 39/12 424/490 |
| 6,655,381 B2 | 12/2003 | Keane et al. | |
| 7,011,818 B2 | 3/2006 | Staniforth | |
| 7,229,645 B2 | 6/2007 | Yuh-Fun et al. | |
| 7,306,787 B2 | 12/2007 | Tarara et al. | |
| 8,968,786 B2 | 5/2015 | Johnston et al. | |
| 9,044,391 B2 | 5/2015 | Williams et al. | |
| 9,061,027 B2 | 6/2015 | Hitt et al. | |
| 9,175,906 B2 | 10/2015 | Scherzer et al. | |
| 9,550,036 B2* | 1/2017 | Hoekman | A61M 15/08 |
| 9,622,974 B2 | 4/2017 | Johnston et al. | |
| 10,092,512 B2 | 10/2018 | Johnston et al. | |
| 10,434,062 B2 | 10/2019 | Johnston et al. | |
| 2003/0064029 A1 | 4/2003 | Tarara et al. | |
| 2003/0090715 A1 | 5/2003 | Yoshikawa | |
| 2003/0232020 A1 | 12/2003 | York et al. | |
| 2004/0042971 A1 | 3/2004 | Carpenter et al. | |
| 2004/0042972 A1 | 3/2004 | Carpenter et al. | |
| 2004/0105821 A1 | 6/2004 | Bernstein et al. | |
| 2004/0137070 A1 | 7/2004 | Scherzer et al. | |
| 2004/0176391 A1 | 9/2004 | Weers et al. | |
| 2006/0228369 A1* | 10/2006 | Chen | A61K 39/39 424/184.1 |
| 2007/0134762 A1 | 6/2007 | Arumugham et al. | |
| 2007/0287675 A1 | 12/2007 | Hitt et al. | |
| 2008/0118442 A1 | 5/2008 | Mohsen et al. | |
| 2009/0208582 A1 | 8/2009 | Johnston et al. | |
| 2010/0158651 A1 | 6/2010 | Randolph | |
| 2010/0221343 A1 | 9/2010 | Johnston et al. | |
| 2011/0195113 A1 | 8/2011 | Richardson et al. | |
| 2011/0280911 A1 | 11/2011 | Myc et al. | |
| 2015/0232855 A1 | 8/2015 | Levitt | |
| 2016/0144023 A1* | 5/2016 | Cui | A61K 9/14 424/490 |
| 2017/0007682 A1* | 1/2017 | Brey | A61K 39/02 |
| 2018/0147161 A1 | 5/2018 | Williams et al. | |
| 2019/0142936 A1 | 5/2019 | Cui et al. | |
| 2021/0170019 A1* | 6/2021 | Cui | A61K 39/12 |
| 2021/0338671 A1 | 11/2021 | Williams et al. | |

FOREIGN PATENT DOCUMENTS

| | | |
|---|---|---|
| WO | WO 2005/025506 | 3/2005 |
| WO | WO 2006/026502 | 3/2006 |
| WO | WO 2008/118691 | 10/2008 |
| WO | WO 2009/103035 | 8/2009 |
| WO | WO 2011/129120 | 4/2011 |
| WO | WO 2011/151760 | 5/2011 |

OTHER PUBLICATIONS

Isaka et al. (Nagoya Medical Journal. 2001; 45(1): 5-15).*
Garmise, Robert J., et al. "Formulation of a dry powder influenza vaccine for nasal delivery." *AAPS PharmSciTech* 7.1 (2006): E131-E137.
Huang, Juan, et al. "A novel dry powder influenza vaccine and intranasal delivery technology: induction of systemic and mucosal immune responses in rats." *Vaccine* 23.6 (2004): 794-801.
International Preliminary Report on Patentability issued in International Application No. PCT/US2018/064837, dated June 25, 2020.
International Search Report and Written Opinion issued in International Application No. PCT/US2018/064837, dated Feb. 21, 2019.
Isaka, Masanori, et al. "Induction of systemic and mucosal antibody responses in mice immunized intranasally with aluminium-non-adsorbed diphtheria toxoid together with recombinant cholera toxin B subunit as an adjuvant." *Vaccine* 18.7 (1999): 743-751.

Maa, Yuh-Fun et al. "Stabilization of Alum-Adjuvanted Vaccine Dry Powder Formulations: Mechanism and Application." Journal of Pharmaceutical Sciences 92.2 (2003): 319-332.
Thakkar, S. (2017). *Novel dry powder formulations of aluminum salt-adjuvanted vaccines for intranasal administration* (Doctoral dissertation).
Ball, Jordan P et al. "Intranasal delivery of a bivalent norovirus vaccine formulated in an in situ gelling dry powder" *PloS one* vol. 12,5 e0177310. May 18, 2017.
Buttini, Francesca, et al. "Particles and powders: tools of innovation for non-invasive drug administration." *Journal of controlled release* 161.2 (2012): 693-702.
Casale, M., et al. "Post-operative nebulized sodium hyaluronate versus spray after functional endoscopic sinus surgery for chronic rhinosinusitis." *Journal of Biological Regulators and Homeostatic Agents* 31.4 supplement 2 (Dec. 2017): 81-89.
Djupesland, Per Gisle. "Nasal drug delivery devices: characteristics and performance in a clinical perspective—a review." *Drug delivery and translational research* 3,1 (2013): 42-62.
Kublik, H., And M. T. Vidgren. "Nasal delivery systems and their effect on deposition and absorption." *Advanced drug delivery reviews* 29.1-2 (1998): 157-177.
Pozzoli, Michele, et al. "Dry powder nasal drug delivery: challenges, opportunities and a study of the commercial Teijin Puvlizer Rhinocort device and formulation." *Drug development and industrial pharmacy* 42.10 (Mar. 2016): 1660-1668.
Braun, L.J. (Mar. 27, 2012). Interactions between antigen and adjuvant. Implications for formulation, 34 pages.
Buitink, Julia, et al. "High critical temperature above Tg may contribute to the stability of biological systems." *Biophysical Journal* 79.2 (2000): 1119-1128.
Chen, D., et al. "Thermostable formulations of a hepatitis B vaccine and a meningitis a polysaccharide conjugate vaccine produced by a spray drying method." *Vaccine* 28.31 (2010): 5093-5099.
Chen, Dexiang, and Debra Kristensen. "Opportunities and challenges of developing thermostable vaccines," *Expert Review of Vaccines* 8.5 (2009): 547-557.
Clausi, Amber L., et al. "Influence of protein conformation and adjuvant aggregation on the effectiveness of aluminum hydroxide adjuvant in a model alkaline phosphatase vaccine." *Journal of Pharmaceutical Sciences* 98.1 (2009): 114-121.
Clausi, Amber L., et al. "Inhibition of aggregation of aluminum hydroxide adjuvant during freezing and drying," *Journal of Pharmaceutical Sciences* 97.6 (2008): 2049-2061.
Clausi, Amber, et al. "Influence of particle size and antigen binding on effectiveness of aluminum salt adjuvants in a model lysozyme vaccine." *Journal of Pharmaceutical Sciences* 97.12 (2008): 5252-5262.
Crowe, Lois M., David S. Reid, and John H. Crowe. "Is trehalose special for preserving dry biomaterials?." *Biophysical Journal* 71.4 (1996): 2087-2093.
Diminsky, Dvorah, et al. "Physical, chemical and immunological stability of CHO-derived hepatitis B surface antigen (HBsAg) particles." *Vaccine* 18.1-2 (1999): 3-17.
Eisenbarth, Stephanie C., et al. "Crucial role for the Nalp3 inflammasome in the immunostimulatory properties of aluminium adjuvants." *Nature* 453.7198 (2008): 1122.
Engstrom, Joshua D., et al. "Formation of stable submicron protein particles by thin film freezing." *Pharmaceutical Research* 25.6 (2008): 1334-1346.
Franchi, Luigi, and Gabriel Núñez. "The Nlrp3 inflammasome is critical for aluminium hydroxide-mediated IL-1β secretion but dispensable for adjuvant activity." *European Journal of Immunology* 38.8 (2008): 2085-2089.
Hem, Stanley L., and Harm HogenEsch. "Relationship between physical and chemical properties of aluminum-containing adjuvants and immunopotentiation." *Expert Review of Vaccines* 6.5 (2007): 685-698.
Hornung, Veit, et al. "Silica crystals and aluminum salts activate the NALP3 inflammasome through phagosomal destabilization." *Nature Immunology* 9.8 (2008): 847.

(56) References Cited

OTHER PUBLICATIONS

Jiang, G. E., et al. "Anthrax vaccine powder formulations for nasal mucosal delivery." *Journal of Pharmaceutical Sciences* 95.1 (2006): 80-96.

Kinsinger, Linda S., et al. "Chemoprevention of breast cancer: a summary of the evidence for the US Preventive Services Task Force." *Annals of internal medicine* 137.1 (2002): 59-69.

Kool, Mirjam, et al. "Cutting edge: alum adjuvant stimulates inflammatory dendritic cells through activation of the NALP3 inflammasome." *The Journal of Immunology* 181.6 (2008): 3755-3759.

Leach, W. Thomas, et al. "Uniform encapsulation of stable protein nanoparticles produced by spray freezing for the reduction of burst release." *Journal of Pharmaceutical Sciences* 94.1 (2005): 56-69.

Méndez, Ilia Z. Romero, et al. "Potentiation of the immune response to non-adsorbed antigens by aluminum-containing adjuvants." *Vaccine* 25.5 (2007): 825-833.

Overhoff, K. A., et al. "Use of thin film freezing to enable drug delivery: a review." *Journal of Drug Delivery Science and Technology* 19.2 (2009): 89-98.

Seeber, Sally J., Joe L. White, and Stanley L. Hem. "Predicting the adsorption of proteins by aluminium-containing adjuvants." *Vaccine* 9.3 (1991): 201-203.

Shi, Yi, Harm HogenEsch, and Stanley L. Hem. "Change in the degree of adsorption of proteins by aluminum-containing adjuvants following exposure to interstitial fluid: freshly prepared and aged model vaccines." *Vaccine* 20.1-2 (2001): 80-85.

Sloat, Brian R., et al. "Strong antibody responses induced by protein antigens conjugated onto the surface of lecithin-based nanoparticles." *Journal of Controlled Release* 141.1 (2010): 93-100.

Tritto, Elaine, Flaviana Mosca, and Ennio De Gregorio. "Mechanism of action of licensed vaccine adjuvants," *Vaccine*27.25-26 (2009): 3331-3334.

Vaccine Excipient & Media Summary, downloaded Mar. 2017 from Centers for Disease Control and Prevention, National Center for Emerging and Zoonotic Infectious Diseases (NCEZID), Division of Healthcare Quality Promotion (DHQP); www.cdc.gov/vaccines/pubs/pinkbook/downloads/appendices/b/excipient-table-2.pdf.

Violette, Philippe D., and Fred Saad. "Chernoprevention of prostate cancer: myths and realities." *The Journal of the American Board of Family Medicine* 25.1 (2012): 111-119.

Wang, Wei. "Lyophilization and development of solid protein pharmaceuticals." *International Journal of Pharmaceutics* 203.1-2 (2000): 1-60.

Watts, Alan B., et al. "Respirable low-density microparticles formed in situ from aerosolized brittle matrices." *Pharmaceutical Research* 30.3 (2013): 813-825.

Wolff, Lena, et al. "Protection of aluminum hydroxide during lyophilisation as an adjuvant for freeze-dried vaccines." *Colloids and Surfaces A: Physicochemical and Engineering Aspects* 330.2-3 (2008), 116-126.

Zapata, Mary I., et al. "Mechanism of freeze-thaw instability of aluminum hydroxycarbonate and magnesium hydroxide gels." *Journal of Pharmaceutical Sciences* 73.1 (1984): 3-8.

Zhang, Meimei, et al. "Formulation and delivery of improved amorphous fenofibrate solid dispersions prepared by thin film freezing." *European Journal of Pharmaceutics and Biopharmaceutics* 82.3 (2012): 534-544.

Abramowitz, et al., "Welding Colloidal Crystals with Carbon Dioxide," Macromolecules (2004) 37:7316-7324.

Adler, et al., "Stability and Surface Activity of Lactate Dehydrogenase in Spray-Dried Trehalose," Journal of Pharmaceutical Sciences (1999) 88(2): 199-208.

Agu, et al., "The lung as a route for systemic delivery of therapeutic proteins and peptides," Respir Res (2001) 2:198-209.

Ashayer, et al., "Investigation of the molecular interactions in a pMDI formulation by atomic force microscopy," European Journal of Pharmaceutical Sciences (2004) 21 :533-543.

Barro, et al., "Rotavirus NSP1 Inhibits Expression of Type I Interferon by Antagonizing the Function of Interferon Regulatory Factors IRF3, IRF5, and IRF7," Journal of Virology (2007) 81(9):4473-4481.

Benfait, "Kos reports achievement of new research and development milestones," Kos Press Release (2004).

Ben-Jebria, et al., "Large Porous Particles for Sustained Protection from Carbachol-Induced Bronchoconstricition in Guinea Pigs," Pharmaceutical Research (1999) 16(4):555-561.

Berlin, et al., "Densities of Several Proteins and L-Amino Acids in the Dry State," J_ Phys. Chem. (1968) 72 (6):1887-1889.

Bevan, M.A., "An Approach to Low-Power, High-Performance, Fast Fourier Transform Processor Design," PhD Dissertation, Carnegie Mellon University, 1999, 186 pages.

Blondino, et al., "Surfactant Dissolution and Water Solubilization in Chlorine-Free Liquified Gas Propellants," Drug Dev. Ind. Pharm., 1998; 24:935-945.

Bodhmage, "Correlation between physical properties and flowability indicators for fine powders", M.S. Thesis, Cept. Chem. Eng., Univ. Saskatchewan, 2006.

Bower, C., et al., "Fractal Morphology of Drug Aggregates in Aerosol Propellant Suspensions," International Journal of Pharmaceutics, (1995), 118:229-235.

Carpenter, et al., "Rational Design of Stable Lyophilized Protein Formulations: Theory and Practice," in: J.F. Carpenter, M.C. Manning (Eds), Pharmaceutical Biotechnology_ 13. Rational Design of Stable Protein Formulations, Kluwer Academic/Plenum Press, New York, 2002, pp. 109-133.

Chow, et al., "Particle Engineering for Pulmonary Drug Delivery," Pharmaceutical Research (2007) 24(3):411-437.

Codrons, et al., "Systemic Delivery of Parathyroid Hormone (1-34) Using Inhalation Dry Powders in Rais," Journal of Pharmaceutical Sciences (2003) 92(5):938-950.

Costantino, et al., "Protein Spray-Freeze Drying. Effect of Atomization Conditions on Particle Size and Stability," Pharmaceutical Research (2000) 17(11):1374-1383.

Courrier, et al., "Pulmonary Drug Delivery Systems: Recent Developments and Prospects," Cril. Rev. Therapeutic Drug Carrier Systems, 2002; 19(4&5):425-498.

De Boer. A. H., et al. "Characterization of inhalation aerosols: a critical evaluation of cascade impactor analysis and laser diffraction technique." *International journal of pharmaceutics*249.1-2 (2002): 219-231.

Dellamary, et al., "Hollow Porous Particles in Metered Dose Inhalers," Pharmaceutical Research (2000) 17 (2):168-174.

Edwards, et al., "Large Porous Particles for Pulmonary Drug Delivery," Science (1997) 276:1868-1871.

Engstrom, et al., "Formation of Stable Submicron Protein Particles by Thin Film Freezing," Pharmaceutical Research (2008) 25(6):1334-1346.

Engstrom, et al., "Morphology of protein particles produced by spray freezing of concentrated solutions," European Journal of Pharmaceutics and Biopharmaceutics (2007) 65:149-162.

Engstrom, et al., "Stable high surface area lactate dehydrogenase particles produced by spray freezing into liquid nitrogen," European Journal of Pharmaceutics and Biopharmaceutics (2007) 65:163-174.

Engstrom, J.D., et al., "Templated Open Flocs of Nanorods for Enhanced Pulmonary Delivery with Pressurized Metered Dose Inhalers," Pharmaceutical Research, (2009), 26:101-117.

Farahnaky, et al., "Enthalpy Relaxation of Bovine Serum Albumin and Implications for its Storage in the Glassy State," Biopolymers (2005) 78:69-77.

Fargues, et al., "Structural characterization of flocs in relation to their settling performances," Chemical Engineering Research and Design 81(A9):1171-1178.

Fargues, et al., "Structural characterization of flocs in relation to their settling performances," (Erratum), Chemical Engineering Research and Design 81(A9):1171-1178.

French, et al., "The influence of formulation on emission, deaggregation and deposition of dry powders for inhalation," J_ Aerosol Sci. (1996) 27(5):769-783.

(56) References Cited

OTHER PUBLICATIONS

Garcia-Contreras, L., et al., "Liquid-Spray or Dry-Powder Systems for Inhaled Delivery of Peptide and Proteins?" Am. J. Drug Delivery, (2005), 3:29-45.

Gonda, I, "Development of a Systematic Theory of Suspension Inhalation Aerosols. I. A Framework to Study the Effects of Aggregation on the Aerodynamic Behaviour of Drug Particles," Int. J. Pharm., 1985; 27:99-116.

Goodarz-Nia, et al., "Floc Simulation. Effects of Particle Size and Shape," Chem. Eng. Sci., 1975; 30:407-12.

Heyder, et al., "Deposition of Particles in the Human Respiratory Tract in the Size Range 0.005-15 mm," J. Aerosol Sci., 1986; 17(5):811-825.

Hilfiker, et al. "Polymorphism in the Pharmaceutical Industry" Wiley-VCH Verlag GmbH & Co., 2006; pp. 1-19 (2006).

Johnson, KA, "Interfacial Phenomena and Phase Behavior in Metered Dose Inhaler Formulations," in: A.J. Hickey (Ed), Inhalation Aerosols: Physical and Biological Basis for Therapy, 2007.

Keller, "Innovations and perspectives of metered dose inhalers in pulmonary drug delivery," International Journal of Pharmaceutics (1999) 186:81-90.

Kim, et al., "Determination of Water in Pressurized Pharmaceutical Metered Dose Aerosol Products," Drug Dev. And Ind. Pharm., 1992; 18(20):2185-95.

Kwon, et al., "Long acting porous microparticle for pulmonary protein delivery," International Journal of Pharmaceutics (2007) 333:5-9.

Labiris, N. R., and M. B. Dolovich. "Pulmonary drug delivery. Part I: physiological factors affecting therapeutic effectiveness of aerosolized medications." *British journal of clinical pharmacology* 56.6 (2003): 588-599.

Lechuga-Ballesteros, et al., "Trileucine Improves Aerosol Performance and Stability of Spray-Dried Powders for Inhalation," Journal of Pharmaceutical Sciences (2008) 97(1):287-302.

Li, et al., "Aerodynamics and aerosol particle deaggregation phenomena in model oral-pharyngeal cavities," J. Aerosol Sci. (1996) 27(8):1269-1286.

Liao, et al., "The effects of polyvinyl alcohol in the in vitro stability and delivery of spray-dried protein particles from surfactant-free HFA 134a-based pressurized metered dose inhalers," International Journal of Pharmaceutics (2005) 304:29-39.

Maa, et al., "Biopharmaceutical Powders: Particle Formation and Formulation Considerations," Curr. Pharm. Biotechnol., 2000; 1(3):283-302.

Maa, et al., "Protein inhalation powders: spray drying vs spray freeze drying," Pharmaceutical Research (1999) 16 (2):249-254.

Maa, et al., Spray freeze-drying of biopharmaceuticals: applications and stability considerations, in: H.R. Costantino, M.J. Pikal (Eds), Biotechnology: Pharmaceutical Aspects. 2. Lyophilization of Biopharmaceuticals, American Association of Pharmaceutical Scientists, Arlington, 2004, pp. 519-561.

Merriam-Webster Online: medical dictionary definitions: atomize, compact, floc, flocculate, flocculent, porous, template. Accessed at http://www.merriam-webster.com/on May 19, 2012.

Nail, et al., "Fundamentals of Freeze-Drying," in: S.L. Nail, M.J. Akers (Eds), Pharmaceutical Biotechnology. 14. Development and Manufacture of Protein Pharmaceuticals, Kluwer Academic/Plenum Publishers, New York, 2002, pp. 281-360.

Nguyen, et al., "Protein Powders for Encapsulation: a comparison of Spray-Freeze Drying and Spray Drying of Darbepoetin Alfa," Pharmaceutical Research (2004) 21(3):507-514.

Oliver, et al., "Initial Assessment of a Protein Formulated in Pressurized Metered Dose Inhalers for Pulmonary Delivery," Respiratory Drug Delivery VII, 2000.

Patton, J.S., et al., "Inhaling Medicines: Delivering Drugs to the Body Through the Lungs," Nature Rev Drug Discovery, (2007), 6:67-74.

PCT/US2009/034162—PCT Search Report & Written Opinion of the International Searching Authority, dated Sep. 22, 2009.

Peguin, et al., "Microscopic and Thermodynamic Properties of the HFA134a-Water Interface: Atomistic Computer Simulations and Tensiometry under Pressure," Langmuir (2006) 22:8826-8830.

Philipse, "The Random Contact Equation and its Implications for (Colloidal) Rods in Packings, Suspensions, and Anisotropic Powders," Langmuir (1996) 12:1127-1133.

Philipse, AP, "The Random Contact Equation and Its Implications for (Colloidal) Rods in Packings, Suspensions, and Anisotropic Powders," (Additions and Corrections), Langmuir, 1996; 12:5971.

Philipse, et al., "On the Density and Structure Formation in Gels and Clusters of Colloidal Rods and Fibers," Langmuir (1998) 14:49-54.

Quinn, et al., "Protein conformational stability in the hydrofluoroalkane propellants tetrafluoroethane and heptafluoropropane analysed by Fourier transform Raman Spectroscopy," International Journal of Pharmaceutics (1999) 186:31-41.

Rogers, et al., "A novel particle engineering technology to enhance dissolution of poorly water soluble drugs: spray-freezing into liquid," European Journal of Pharmaceutics and Biopharmaceutics (2002) 54:271-280.

Rogers, et al., "Micronized powders of a poorly water soluble drug produced by a spray-freezing into liquid-emulsion process," European Journal of Pharmaceutics and Biopharmaceutics (2003) 55:161-172.

Rogueda, "HPFP, a Model Propellant for pMD1s," Drug Development and Industrial Pharmacy (2003) 29(1):39-49.

Rogueda, "Novel hydrofluoroalkane suspension formulations for respiratory drug delivery," Expert Opinion Drug Del. (2005) 2:625-638.

Sakagami. "In vivo, in vitro and ex vivo models to assess pulmonary absorption and disposition of inhaled therapeutics for systemic delivery." *Advanced drug delivery reviews* 58.9-10 (2006): 1030-1060.

Shekunov, et al., "Particle size analysis in pharmaceutics: principles, methods and applications," Pharmaceutical Research (2007) 24(2):203-227.

Shoyele, et al., "Prospects of formulating proteins/peptides as aerosols for pulmonary drug delivery," International Journal of Pharmaceutics (2006) 314:1-8.

Sigma Aldrich catalog entry: itraconazole. Accessed on Oct. 11, 2011 at <http://www.sigmaaldrich.com/catalog/Lookup.do?N3=mode+matchpartialmax&N4-itraconacole&D7=0&D10=itraconazole&N1=S_ID&ST=RS&N25=O&F=PR>.

Smith, et al., "Electrostatically Stabilized Metal Oxide Particle Dispersions in Carbon Dioxide," J. Phys. Chem. B (2005) 109:20155-20165.

Smyth, et al., "Aerosol Generation from Propellant-Driven Metered Dose Inhalers," in: J. Hickey Anthony (Ed), Inhalation Aerosols: Physical and Biological Basis for Therapy, 2007, pp. 399-416.

Steckel, et al., "In vitro evaluation of dry powder inhalers I: drug depostition of commonly used devices," International Journal of Pharmaceutics (1997) 154:19-29.

Stein, S.W., et al., "The Relative Influence of Atomization and Evaporation on Metered Dose Inhaler Drug Delivery Efficiency," Aerosol Science and Technology, (2006), 40:335-347.

Tadmor, "The London-van der Waals interaction energy between objects of various geometries," J. Phys.: Condens. Matter(2001) 13:L195-L202.

Takashima, et al., "A Study of Proton Fluctuation in Protein. Experimental Study of the Kirkwood-Shumaker Theory," the Journal of Physical Chemistry (1965) 69(7):2281-2286.

Tam, et al., "Amorphous Cyclosporin Nanodispersions for Enhanced Pulmonary Deposition and Dissolution," Journal of Pharmaceutical Sciences (2008) 97(11):4915-4933.

Tang, et al., "A Model to Describe the Settling Behavior of Fractal Aggregates," Journal of Colloid and Interface Science (2002) 247:210-219.

Traini, et al., "In Vitro Investigation of Drug Particulates Interactions and Aerosol Performance of Pressurised Metered Dose Inhalers," Pharmaceutical Research (2007) 21(1):125-135.

Traini, et al., "Surface Energy and Interparticle Force Correlation in Model pMDI Formulations," Pharmaceutical Research, (2005) 22(5):816-825.

(56) References Cited

OTHER PUBLICATIONS

Traini, et al., "The Use of AFM and Surface Energy Measurements to Investigate Drug-Canister Material Interactions in a Model Pressurized Metered Dose Inhaler Formulation," Aerosol Science and Technology (2006) 40:227-236.

Tsapis, et al., "Trojan particles: Large Porous Carriers of Nanoparticles for Drug Delivery," PNAS (2002) 99 (19):12001-12005.

Ulrich, DR, "Chemical Processing of Ceramics," Chem. Eng. News, 1990; 68:28-40.

US Pharmacopeia Ch. 1174: Powder Flow, 2004.

Vanbever, et al., "Formulation and Physical Characterization of Large Porous Particles for Inhalation," Pharmaceutical Research (1999) 16(11):1735-1742.

Vervaet, et al., "Drug-surfactant-propellant interactions in HFA-formulations," International Journal of Pharmaceutics (1999) 186:13-30.

Watts, "Pulmonary Delivery of Tacrolimus for Lung Transplant and Asthma Therapy," Ph.D. Dissertation, The University of Texas at Austin, 2009.

Webb, et al., A New Mechansim for Decreasing Aggregation of Recombinant Human Interferon-γ by a Surfactant Slowed Dissolution of Lyophilized Formulations in a Solution Containing 0.03% Polysorbate 20.

Webb, et al., "Surface Adsorption of Recombinant Human Interferon-γ in Lyophilized and Spray-Lyophilized Formulations," Journal of Pharmaceutical Sciences (2002) 91(6):1474-1487.

White, et al., "EXUBERA: Pharmaceutical Development of a Novel Product for Pulmonary Delivery of Insulin," Diabetes Technology & Therapeutics (2005) 7:896-906.

Williams, et al., "Formulation of a protein with a propellant HFA 134a for aerosol delivery," European Journal of Pharmaceutical Sciences (1998) 7:137-144.

Williams, et al., "Influence of Metering Chamber Volume and Water Level on the Emitted Dose of a Suspension-Based pMDI Containing Propellant 134a," Pharmaceutical Research (1997) 14(4):438-443.

Williams, III, et al., "Influence of Propellant Composition on Drug Delivery from a Pressurized Metered-Dose Inhaler," Drug Dev. Ind. Pharm., 1998; 24(8):763-770.

Wu, et al., "Molecular Scale Behavior in Alternative Propellant-Based Inhaler Formulations," in: A.J. Hickey (Ed), Inhalation Aerosols: Physical and Biological Basis for Therapy, 2007.

Yu, et al., "Preparation and characterization of microparticles containing peptide produced by a novel process: spray freezing into liquid," European Journal of Pharmaceutics and Biopharmaceutics (2002) 54:221-228.

Yu, et al., "Spray freezing into liquid nitrogen for highly stable protein nanostructured microparticles," European Journal of Pharmaceutics and Biopharmaceutics (2004) 58:529-537.

Yu, et al., "Spray freezing into liquid versus spray-freeze drying: Influence of atomization on protein aggregation and biological activity," European Journal of Pharmaceutical Sciences (2006) 27:9-18.

Zhanpeng, J., et al., "Flocculation Morphology: Effect of Particulate shape and Coagulant Species on Flocculation," Water Sci Technol., (2006), 53:9-16.

Butler, W T et al. "Effect of physical state and route of inoculation of diphtheria toxoid on the formation of nasal secretory and serum antibodies in man." *Journal of immunology (Baltimore, Md. : 1950)* vol. 104,6 (1970): 1396-400.

Madhavan, Meera et al. "Tolerability and immunogenicity of an intranasally-administered adenovirus-vectored COVID-19 vaccine: An open-label partiaily-randomised ascending dose phase I trial." *EBioMedicine* vol. 85 (2022): 104298.

\* cited by examiner

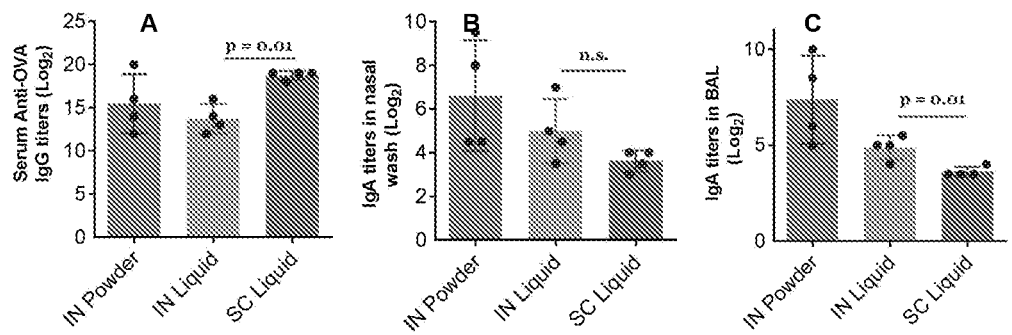
FIG. 4
(A) IN TFFD
(B) SC Liquid
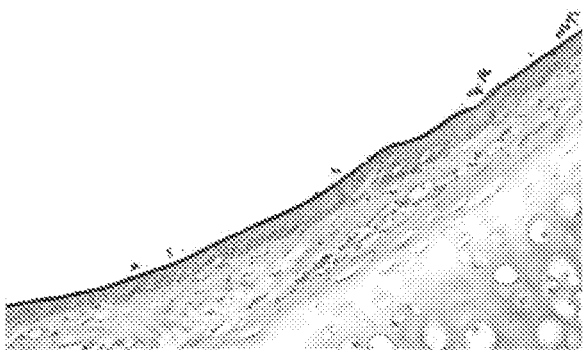

(C) IN Liquid

(D) Saline

DRY ADJUVANTED IMMUNE STIMULATING COMPOSITIONS AND USE THEREOF FOR MUCOSAL ADMINISTRATION

This application is a national phase application under 35 U.S.C. § 371 of International Application No. PCT/US2018/064837, filed Dec. 11, 2018, which claims the benefit of U.S. Provisional Patent Application No. 62/597,037, filed Dec. 11, 2017, the entirety of each of which is incorporated herein by reference.

This invention was made with government support under Grant no. R21 AI105789 awarded by the National Institutes of Health. The government has certain rights in the invention.

BACKGROUND OF THE INVENTION

1. Field of the Invention

The present invention relates generally to the field of medicine and immunology. More particularly, it concerns aluminum adjuvant dry powder formulations and their use immune stimulation by nasal administration.

2. Description of Related Art

Adjuvants are frequently needed for newer generation vaccines, such as protein subunit vaccines, to elicit a strong immune response. Aluminum-containing compounds such as aluminum hydroxide and aluminum phosphate have been used as human vaccine adjuvants for decades. Some insoluble aluminum salts, e.g. aluminum (oxy)hydroxide and aluminum (hydroxy)phosphate, are used in many currently licensed vaccines as adjuvants and possess excellent safety profiles (O'Hagan et al., 2001; Singh and O'Hagan, 1999). A major limitation with aluminum salt-adjuvanted vaccines is that they must be maintained in cold-chain (2-8° C.) during transport and storage (Milstien et al., 2006). However, a troubling problem with these vaccines is that they must not be frozen because slow freezing of the dispersion causes irreversible coagulation that damages the vaccines. Vaccines that have been inadvertently exposed to freezing conditions before being administered to patients must be discarded, causing significant product waste and limited utility. This is significant considering that this cold-chain storage alone accounts for up to 80% of the financial costs of vaccination (Chen et al., 2011, J Control. Rel., 152: 412-8), and complicating matters further, an estimated 75-100% of the vaccine shipments are actually exposed to freezing temperatures (Matthias et al., Vaccine, 2007, 25: 3980-6), resulting in costly waste and the loss of nearly half of all global vaccine supplies (WHO data). It has previously been shown that thin-film freeze-drying (TFFD) can be used to convert aluminum salt-adjuvanted vaccines from liquid to dry powder without causing particle aggregation or decreasing the immunogenicity following reconstitution (Li et al., 2015; Thakkar et al., 2017; U.S. patent application Ser. No. 14/941,323). Importantly, the resultant dry powder vaccine can be stored in temperatures as high as 40° C. for an extended period of time (Thakkar et al., 2017).

Aluminum salt-adjuvanted vaccines are generally administered by subcutaneous, intradermal, or intramuscular injection. However, reconstituting the dry powder vaccine before injection has various limitations such as the need for sterile water for injection, the need for trained medical personnel, and the increased chance of error made when reconstituting the powder and filling syringes. The nasal route for immunization offers some interesting opportunities. Almost all infectious agents enter the body through the mucosal surfaces (Mestecky et al., 1997), and the nasal mucosa is often the first point of contact for inhaled pathogens. Therefore, ideally, to more effectively protect against inhaled pathogens, vaccines should be administered via the nasal mucosal surface to induce mucosal immunity to prevent infectious agents from entering the host (Davis et al., 2001). Besides enabling vaccines to induce both mucosal and systemic immune responses (Hashigucci et al., 1996; Smith et al., 2003), intranasal immunization has several other advantages as well. For example, the nose tissue is easily accessible and highly vascularized, and can be used in the case of epidemics for mass vaccination. In addition, nasal immunization enables needle-free, non-invasive delivery of vaccines with the possibility of self-immunization.

It is evident that having aluminum-containing vaccines in a solid form, and for needle-free administration, would be hugely beneficial to the modern healthcare system. However, it had been previously thought that aluminum salt-based adjuvants are not capable of potentiating mucosal immune responses when given intranasally.

SUMMARY OF THE INVENTION

In some embodiments, the present disclosure provides a method for stimulating an immune response in a patient, comprising intranasally administering to the patient a dry powder composition comprising an antigenic polypeptide adsorbed to an aluminum adjuvant. In some aspects, at least 75, 80, 85, 90, 91, 92, 93, 94, 95, 96, 97, 98, or 99% of said antigenic protein is adsorbed to the aluminum adjuvant. In some aspects, at least 60% of said antigenic protein is not denatured. In some aspects, at least 70% of said antigenic protein is not denatured. In some aspects, at least 75, 80, 85, 90, 91, 92, 93, 94, 95, 96, 97, 98, or 99% of said antigenic protein is not denatured.

In further embodiments, there is provided a method for stimulating an immune response in a patient, comprising: (a) obtaining a dry powder composition comprising an antigenic polypeptide adsorbed to an aluminum adjuvant; (b) suspending the dry power in pharmaceutically acceptable liquid to form a suspension; and (c) intranasally administering the suspension to the patient. In still further aspects, a method can comprise obtaining powder composition comprising an antigenic polypeptide adsorbed to an aluminum adjuvant, wherein the powder is comprised in a liquid suspension; and intranasally administering the suspension to the patient. In some aspects, a pharmaceutically acceptable liquid for use according to the embodiments comprises sterile water or saline solution.

In some aspects, said aluminum adjuvant is aluminum hydroxide. In some aspects, said aluminum adjuvant is aluminum phosphate. In some aspects, said aluminum adjuvant is potassium aluminum sulfate.

In some aspects, the dry powder composition comprises less than 5% water. In some aspects, the dry powder composition comprises less than 4% water. In some aspects, the dry powder composition comprises less than 3% water. In some aspects, the dry powder composition comprises less than 2% water. In some aspects, the dry powder composition comprises less than 1% water. In some aspects, the dry powder composition is essentially free of water. In some aspects, the dry powder composition is prepared from a liquid composition.

In certain aspects, a dry powder composition (or a powder suspension) of the embodiments is composed of particles having an average diameter of 0.1 to 100 μm. For example, the powder can have an average diameter 1.0 to 100 μm, 1 to 50 μm, 5 to 20 μm or 5 to 15 μm.

In some aspects, the dry powder composition further comprises an excipient. In some aspects, the excipient is a salt. In some aspects, the excipient is a sugar. In some aspects the excipient is a buffer. In some aspects, the excipient is a detergent. In some aspects the excipient is a polymer. In some aspects, the excipient is an amino acid. In some aspects, the excipient is a preservative. In some aspects, the excipient is disodium edetate, sodium chloride, sodium citrate, sodium succinate, sodium hydroxide, sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benzyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminophenyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer. In some aspects, said excipient is trehalose.

In certain aspects, a dry powder composition of the embodiments comprises from about 50% to about 99% (e.g. 60%, 70%, 80%, or 90% to 99%) wt/wt of an excipient. In some other aspects, the dry powder composition comprises less than 3% wt/wt of an excipient. In some aspects, the dry powder composition comprises less than 2% wt/wt of an excipient. In some aspects, the dry powder composition comprises less than 1% wt/wt of an excipient. In some aspects, the dry powder composition is essentially free of excipients. In some aspects, the dry powder composition is free of excipients.

In some aspects, the method for stimulating an immune response in a patient is a method of stimulating an immune response against diphtheria, tetanus, pertussis, influenza, pneumonia, otitis media, bacteremia, meningitis, hepatitis, cirrhosis, anthrax poisoning, rabies, warts, poliomyelitis, Japanese encephalitis, or cancer.

In some aspects, the dry powder composition comprises an antigenic polypeptide is from an infectious agent. In some aspects, the infectious agent is *Clostridium tetani, Streptococcus pneumonia*, Hepatitis A, Hepatitis B, *Haemophilus* influenza, *Corynebacterium diphtheria, Bordetella pertussis, Human papillomavirus, Bacillus anthracis*, Rabies virus, Japanese encephalitis virus, or Poliovirus. In still further aspects, the antigenic polypeptide is from an infectious agent.

In some aspects, the method of stimulating an immune response in a patient is further defined as a method of treating or preventing a disease in a patient in need thereof. In some aspects, the method of preventing a disease may prevent diphtheria, tetanus, pertussis, influenza, pneumonia, otitis media, bacteremia, meningitis, hepatitis, cirrhosis, anthrax poisoning, rabies, warts, poliomyelitis, Japanese encephalitis, or cancer.

In some aspects, intranasal administration comprises inhalation of the dry powder composition. In some aspects, the dry powder composition is administered using an inhaler. In some aspects, the inhaler comprises a pressurized canister. In some aspects, the inhaler comprises a pump bottle. In some aspects, the inhaler comprises a syringe.

In some embodiments, the present disclosure provides a nasal spray comprising a vessel comprising dry powder composition comprises an antigenic polypeptide adsorbed to an aluminum adjuvant; and an applicator capable of dispersing the dry powder composition into the nasal cavity. In some aspects, the applicator comprises a pressurized canister. In some aspects, the applicator comprises a pump bottle. In some aspects, the applicator comprises a syringe.

In some embodiments, the present disclosure provides a kit comprising a dry powder composition and an applicator capable of dispersing the dry powder composition into the nasal cavity, wherein the dry powder composition comprises an antigenic peptide adsorbed to an aluminum adjuvant.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1B:
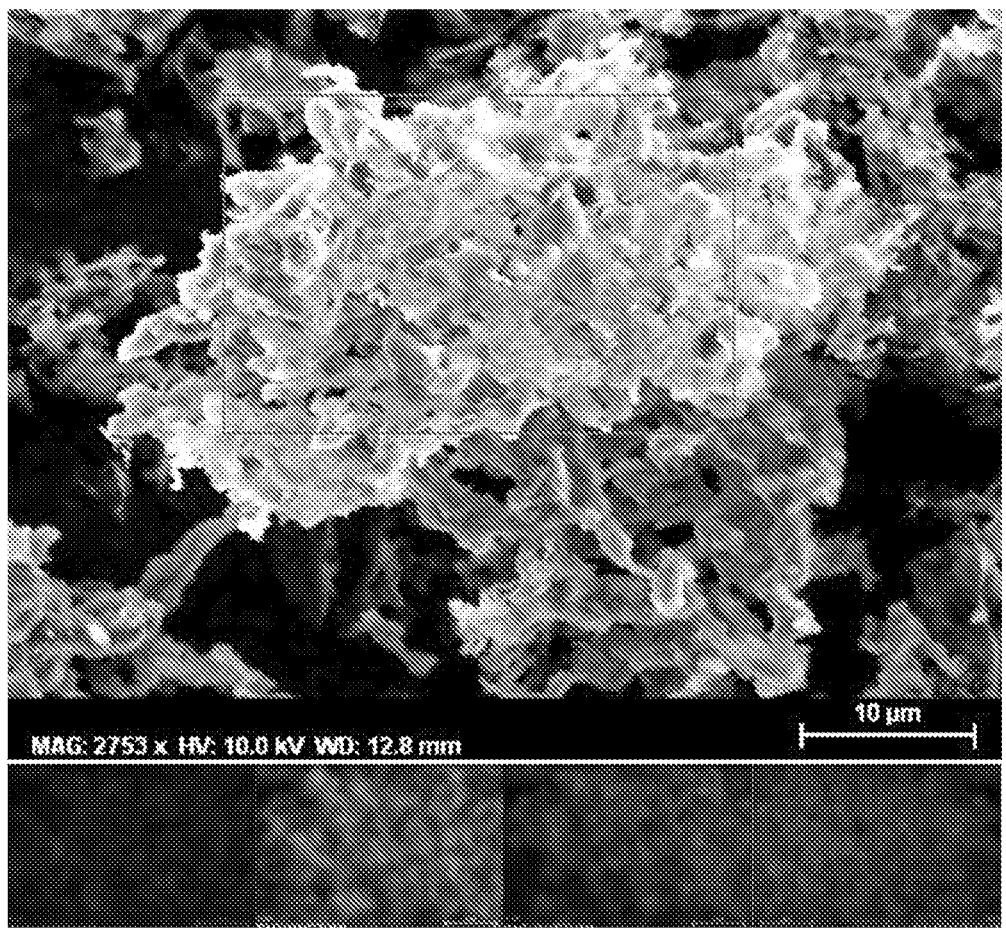
Figure 1C:
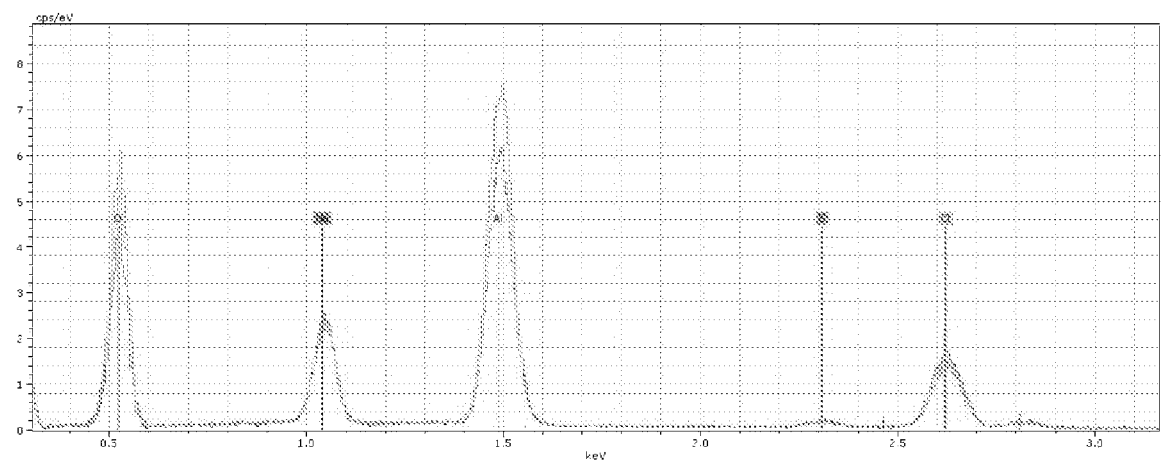

FIG. 1A-C: SEM/EDS of dry powder vaccine. Shown in (A) are representative SEM images of the dry powder vaccine at different magnifications. (B) Randomly selected area in a SEM graph (upper panel), and representative elemental mapping (bottom panel). (C) EDS spectra of the elements tested (Al, O, Na, Cl; n=3 random areas).

Figure 2A:
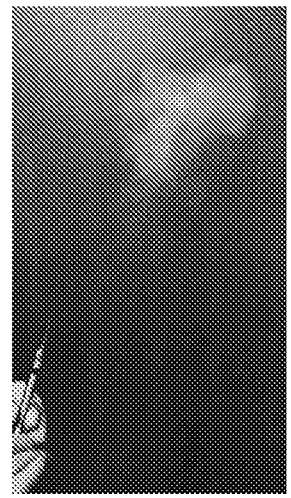
Figure 2B:
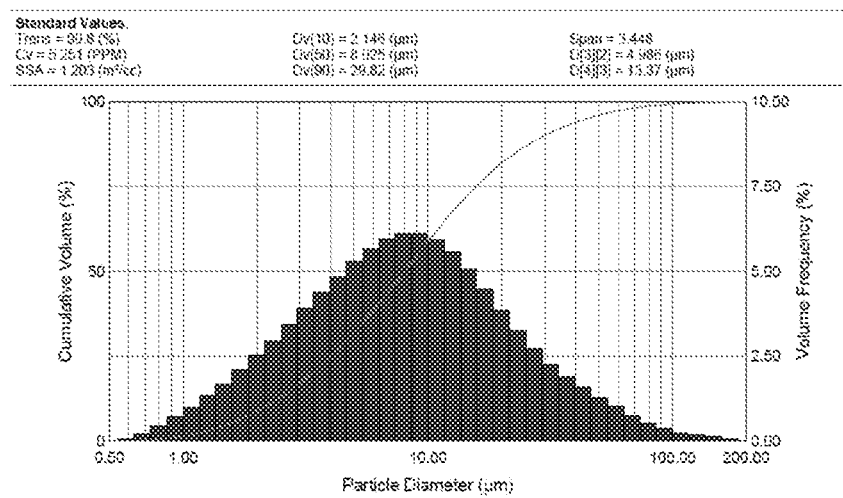

FIG. 2A-B: Dry powder vaccine dispersion. (A) Dry powder vaccine powder cloud evolving from the nasal dry powder delivery device. (B) A representative particle size distribution curves of the dry powder vaccine determined by Malvern Spraytec®.

Figure 3A:
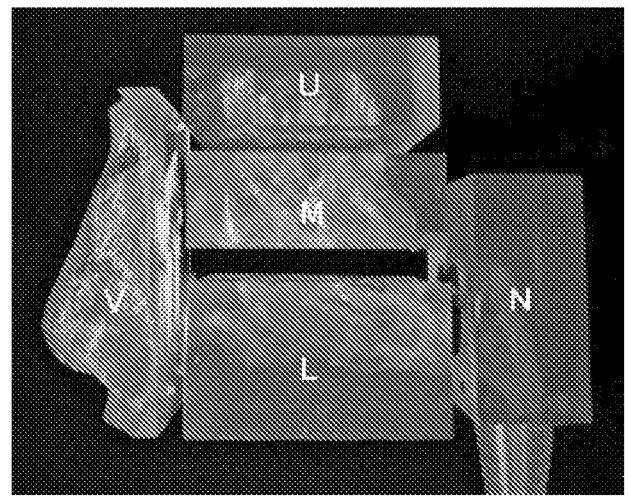
Figure 3B:
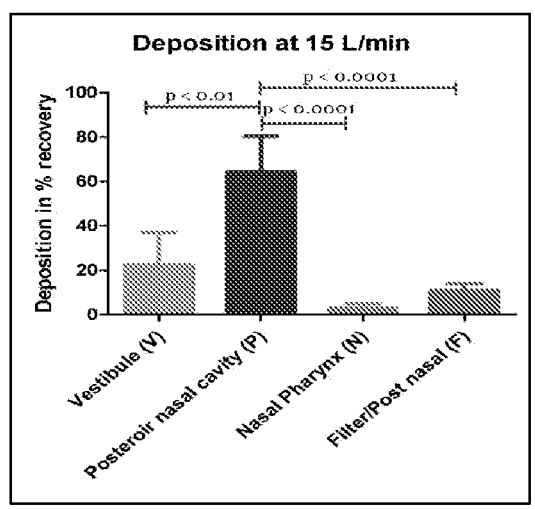

FIG. 3A-B: (A) A diagram of the different sections of the nasal cast used. A—Anterior region making up the vestibule (V) and nasal valve area; U, M, L—upper, middle and lower turbinate regions, collectively called posterior nasal cavity (P); N—nasopharynx; and F—post-nasal fraction. (B) Deposition of the dry powder vaccine in nasal casts operated at 15 L/min. Data are mean±S.D. from 5 adult casts. * $p<0.0001$, posterior nasal cavity (P) vs. Nasopharynx (N), * $p<0.0001$, posterior nasal cavity (P) vs. Filter/post nasal (F), and * $p<0.01$, posterior nasal cavity (P) vs. vestibule (V).

FIG. 4: Serum anti-OVA IgG titers and mucosal IgA titers in rats immunized with dry powder vaccine intranasally. Rats were dosed on days 0, 14 and 28 with the dry powder vaccine intranasally (IN Powder, n=4), the liquid vaccine intranasally (IN Liquid, n=4), or subcutaneously with the liquid vaccine (SC Liquid, n=4). The dose of OVA was 20 μg per rat, and 400 μg for Alhydrogel®, in the IN Liquid and SC Liquid groups. In the IN Powder group, the dose of OVA in the first immunization was 21.6+/−3.0 mcg/rat. However, in the second and third immunizations, largely because the amount of dry powder that came out of the nasal dry powder delivery device varies each time, some rats were dosed twice, leading to an increase in the dose of OVA to more than 20 mcg/rat (i.e. 49.4+/−6.6 mcg/rat and 85.7+/−19.5 mcg/rat, respectively). The anti-OVA IgG titers in serum samples (A), OVA-specific IgA titers in the nasal washes (B) and BAL samples (C) were measured 28 days after the third immunization. In (A), $p=0.001$, IN Liquid vs SC Liquid. In (B), n.s., not significant; in (C), $p=0.01$, IN Liquid vs SC Liquid.

Figure 5:
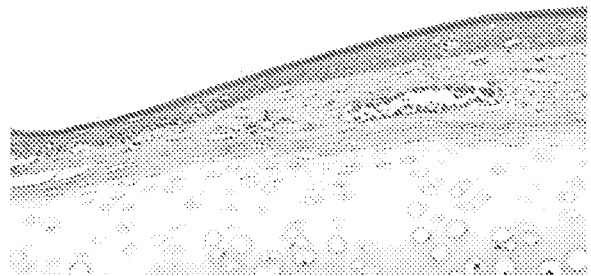
Figure 5:
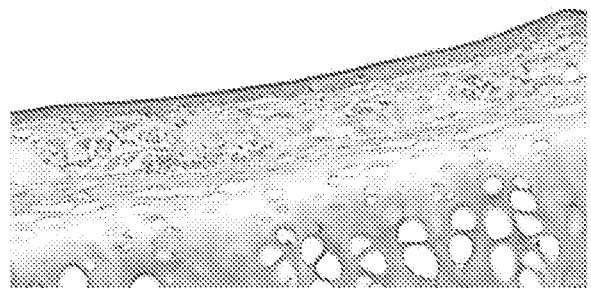

FIG. 5: Representative histological pictures of rat nasal epithelium. Shown are H&E stained images of the rats intranasally dosed with dry powder vaccine (IN Powder) (A), s.c. dosed with liquid vaccine (SC Liquid)) (B), intranasally dosed with liquid vaccine (IN Liquid) (C), or intranasally dosed with normal saline (Saline) (D).

Figure 6:
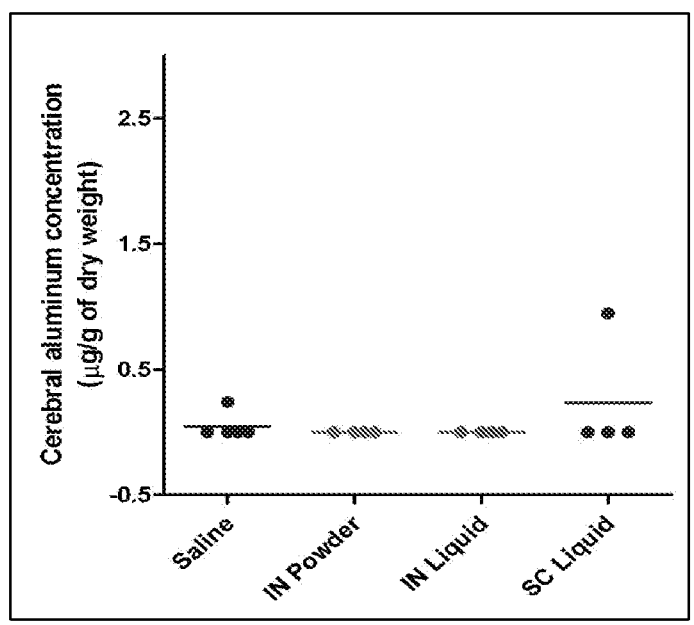

FIG. 6: Aluminum levels determined in rat brain tissues (μg/g of dry weight). Brain was collected 28 days after the third immunization, desiccated, and then incinerated before determining aluminum content in the samples using ICP-MS.

DESCRIPTION OF ILLUSTRATIVE EMBODIMENTS

I. The Present Embodiments

Described herein is an aluminum salt-adjuvanted dry powder immunogenic composition, as well as methods of preparation, and methods of immunization with the aluminum salt-adjuvanted composition The method of preparation, in some aspects, comprises freezing aluminum-containing immunogenic compositions (e.g., with a very low percentage cryoprotectant(s)) such that when converted into a dried powder, the solid can be readily used as an inhalable immunogenic composition. The solid form of the compositions may now be transported and stored in a wide range of temperatures without concern of accidental exposure to freezing conditions. In addition, the solid form of an immunogenic composition may also be stored at room temperature, which will potentially decrease the costs of vaccines. Further, the composition requires no reconstitution, thereby decreasing handling errors and further decreasing the cost.

II. Definitions

The abbreviations used herein have their conventional meaning within the chemical and biological arts. Description of compounds of the present embodiments is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat a disease associated with (e.g. caused by) an infectious agent (e.g. bacterium or virus). The term "treating" and conjugations thereof, include prevention of an injury, pathology, condition, or disease. The term "preventing" or "prevention" refers to any indicia of success in protecting a subject or patient (e.g. a subject or patient at risk of developing a disease or condition) from developing, contracting, or having a disease or condition (e.g. an infectious disease or diseases associated with an infectious agent), including preventing one or more symptoms of a disease or condition or diminishing the occurrence, severity, or duration of any symptoms of a disease or condition following administration of a prophylactic or preventative composition as described herein.

An "effective amount" is an amount sufficient for a composition (e.g. compound, vaccine, drug) to accomplish a stated purpose relative to the absence of the composition (e.g. compound, vaccine, drug) (e.g. achieve the effect for which it is administered, treat a disease (e.g. reverse or prevent or reduce severity), reduce spread of an infectious disease or agent, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a composition (e.g., an immunogenic composition) is an amount of a composition that, when administered to a subject, will have the intended prophylactic effect, e.g., preventing or delaying the onset (or reoccurrence) of an injury, disease (e.g. infectious disease), pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses (e.g. prime-boost). Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of infection or one or more symptoms of infection in the absence of a composition (e.g. an immunogenic composition) as described herein (including embodiments).

"Contacting" is used in accordance with its plain ordinary meaning and refers to the process of allowing at least two distinct species (e.g. compositions, bacterium, virus, biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a composition (e.g. an immunogenic composition) as described herein and a cell, virus, virus particle, protein, enzyme, or patient. In some embodiments contacting includes allowing a composition described herein to interact with a protein or enzyme that is involved in a signaling pathway. In some embodiments contacting includes allowing a composition described herein to interact with a component of a subject's immune system involved in developing immunity to a component of the composition.

As defined herein, the term "inhibition", "inhibit", "inhibiting" and the like in reference to a protein-inhibitor or interaction means negatively affecting (e.g. decreasing) the activity or function of the protein. In some embodiments inhibition refers to reduction of a disease or symptoms of disease. In some embodiments inhibition refers to reduction of the growth, proliferation, or spread of an infectious agent (e.g. bacterium or virus). In some embodiments inhibition refers to preventing the infection of a subject by an infectious agent (e.g. bacterium or virus). In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating the signaling pathway or enzymatic activity or the amount of a protein.

The term "modulator" refers to a composition that increases or decreases the level of a target (e.g. molecule, cell, bacterium, virus particle, protein) or the function of a target or the physical state of the target.

The term "modulate" is used in accordance with its plain ordinary meaning and refers to the act of changing or varying one or more properties. "Modulation" refers to the process of changing or varying one or more properties. For example, as applied to the effects of a modulator on a target, to modulate means to change by increasing or decreasing a property or function of the target or the amount of the target.

"Patient" or "subject in need thereof" refers to a living organism suffering from or prone to a disease or condition that can be treated by administration of a composition (e.g. an immunogenic composition or pharmaceutical composition) as provided herein. Non limiting examples include humans, other mammals, bovines, rats, mice, dogs, monkeys, goat, sheep, cows, deer, and other non mammalian animals. In some embodiments, a patient is human. In some embodiments, a patient or subject in need thereof, refers to a living organism (e.g. human) at risk of developing, contracting, or having a disease or condition associated with an infectious agent (e.g. bacterium or virus).

"Disease" or "condition" refer to a state of being or health status of a patient or subject capable of being treated with the compositions (e.g. an immunogenic compositions) or methods provided herein. In some embodiments, the disease is a disease related to (e.g. caused by) an infectious agent (e.g. bacterium or virus).

"Pharmaceutically acceptable excipient" and "pharmaceutically acceptable carrier" refer to a substance that aids the administration of an active agent to or absorption by a subject and can be included in the compositions of the present embodiments without causing a significant adverse toxicological effect on the patient. Non limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compositions of the embodiments. One of skill in the art will recognize that other pharmaceutical excipients are useful in the embodiments. In embodiments, an excipient is a salt, sugar (saccharide), buffer, detergent, polymer, amino acid, or preservative. In embodiments, the excipient is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benzyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminophenyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer.

The term "preparation" is intended to include the formulation of the active compound with encapsulating material as a carrier providing a capsule in which the active component with or without other carriers, is surrounded by a carrier, which is thus in association with it.

As used herein, the term "intranasally administering" means administration such that the majority of the administered composition is deposited in the nasal cavity, and preferably in contact with nasal epithelium. Thus, in some aspects, intranasal administration is directly applied through the nostrils and results in minimal deposition of administered compositions in the mouth, throat or lungs of a subject. In certain aspects, a composition is selectively deposited in the posterior nasal cavity of a subject.

By "co-administer" it is meant that a composition described herein is administered at the same time, just prior to, or just after the administration of one or more additional therapies, for example infection therapies such as antiviral drugs or an immunogenic composition (e.g., including a different antigen). The compositions (e.g. immunogenic compositions) of the embodiments can be administered alone or can be coadministered to the patient. Co-administration is meant to include simultaneous or sequential administration of the compounds individually or in combination (more than one composition) and includes immunogenic composition administration in a prime-boost method. Thus, the preparations can also be combined, when desired, with other active substances (e.g. to reduce metabolic degradation, increase immune response (e.g. adjuvant)). The compositions of the present embodiments can be delivered by transdermally, by a topical route, transcutaneously, formulated as solutions, suspensions, emulsions, gels, creams, ointments, pastes, jellies, paints, powders, and aerosols.

The term "administer (or administering) a composition" means administering a composition that prevents or treats an infection in a subject. Administration may include, without being limited by mechanism, allowing sufficient time for the immunogenic composition to induce an immune response in the subject or to reduce one or more symptoms of a disease.

The terms "peptide," "polypeptide," and "protein" are used interchangeably herein to refer to a polymer of amino acid residues. An "antigenic protein" is a protein that may be included in an immunogenic composition as an antigen. In embodiments, an antigenic protein may be an antigenic protein conjugated to a sugar (i.e. saccharide) (e.g. monosaccharide, disaccharide, polysaccharide) "antigenic protein saccharide conjugate". In embodiments, an antigenic protein may be an antigenic protein that is not conjugated to a sugar (saccharide).

The term "peptidyl" and "peptidyl moiety" means a monovalent peptide.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

The terms "dose" and "dosage" are used interchangeably herein. A dose refers to the amount of active ingredient given to an individual at each administration. For the present methods and compositions provided herein, the dose may generally refer to the amount of disease treatment. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

The term "adjuvant" is used in accordance with its plain ordinary meaning within Immunology and refers to a substance that is commonly used as a component of an immunogenic composition. Adjuvants may increase an antigen specific immune response in a subject when administered to the subject with one or more specific antigens as part of an immunogenic composition. In some embodiments, an adjuvant accelerates an immune response to an antigen. In some embodiments, an adjuvant prolongs an immune response to an antigen. In some embodiments, an adjuvant enhances an immune response to an antigen. In some embodiments, an adjuvant is an aluminum adjuvant.

Immunogenic composition compositions typically include an adjuvant, regardless of the nature of the agent. An adjuvant stimulates the immune system and increases the response of the immune system to the agent present in the immunogenic composition. Most adjuvants used in vaccines in the United States are aluminum salts. Examples of aluminum salts include, but are not limited to: aluminum phosphate, aluminum hydroxide, aluminum sulfate, and aluminum potassium sulfate.

The term "aluminum adjuvant" refers to an adjuvant including aluminum. In some embodiments, an aluminum adjuvant includes aluminum (oxy)-hydroxide. In some embodiments, an aluminum adjuvant is aluminum (oxy) hydroxide. In some embodiments, an aluminum adjuvant includes aluminum phosphate. In some embodiments, an aluminum adjuvant is aluminum (hydroxy)phosphate. In some embodiments, an aluminum adjuvant includes potassium aluminum sulfate. In some embodiments, an aluminum adjuvant is potassium aluminum sulfate. In some embodiments, an aluminum adjuvant includes aluminum sulfate. In some embodiments, an aluminum adjuvant is aluminum sulfate. In some embodiments, an aluminum adjuvant is aluminum (oxy)hydroxide adjuvant. In some embodiments, an aluminum adjuvant is aluminum (hydroxy)phosphate adjuvant. In some embodiments, an aluminum adjuvant is potassium aluminum sulfate adjuvant. In some embodiments, an aluminum adjuvant is Alum. In some embodiments, an aluminum adjuvant is CAS no. 21645-51-2. In some embodiments, an aluminum adjuvant is aluminum hydroxide gel. In some embodiments, an aluminum adjuvant is aluminum hydroxide gel in the form of a white gelatinous precipitate. In some embodiments, an aluminum adjuvant is CAS no. 7784-30-7. In some embodiments, an aluminum adjuvant is aluminum phosphate gel. In some embodiments, an aluminum adjuvant is aluminum phosphate gel in the form of a white gelatinous precipitate. In some embodiments, an aluminum adjuvant is Imject Alum Adjuvant™. In some embodiments, an aluminum adjuvant is aluminum hydroxide without magnesium hydroxide. In some embodiments, an aluminum adjuvant is Alhydrogel®. In some embodiments, an aluminum adjuvant is Adju-Phos™. In some embodiments, an aluminum adjuvant is Adjuphos™. In some embodiments, an aluminum adjuvant is amorphous aluminum hydroxide and not crystalline aluminum hydroxide. In some embodiments, an aluminum adjuvant includes amorphous aluminum and not crystalline aluminum. In some embodiments, aluminum adjuvant is crystalline aluminum hydroxide and not amorphous aluminum hydroxide. In some embodiments, an aluminum adjuvant includes crystalline aluminum and not amorphous aluminum. In some embodiments, an aluminum adjuvant includes crystalline aluminum oxyhydroxide. In some embodiments, an aluminum adjuvant is crystalline aluminum oxyhydroxide. In some embodiments, an aluminum adjuvant includes amorphous aluminum hydroxyphosphate. In some embodiments, an aluminum adjuvant is amorphous aluminum hydroxyphosphate. In some embodiments, an aluminum adjuvant includes aluminum oxyhydroxide and not aluminum hydroxycarbonate. In some embodiments, an aluminum adjuvant is aluminum oxyhydroxide and not aluminum hydroxycarbonate. In some embodiments, an aluminum adjuvant includes aluminum oxyhydroxide and not magnesium hydroxide. In some embodiments, an aluminum adjuvant is aluminum oxyhydroxide and not magnesium hydroxide. In some embodiments, an aluminum adjuvant does not include amorphous aluminum hydroxide in which some hydroxyls are replaced by sulfate anions. In some embodiments, an aluminum adjuvant includes aluminum oxyhydroxide in a Boehmite-like pattern. In some embodiments, an aluminum adjuvant is aluminum oxyhydroxide in a Boehmite-like pattern. In some embodiments of an aluminum adjuvant described above, the description is of the aluminum adjuvant prior to inclusion in a vaccine. In some embodiments, an aluminum adjuvant is an aluminum containing adjuvant approved by the FDA for administration to humans. In some embodiments, an aluminum adjuvant is an aluminum hydroxide adjuvant approved for administration to humans by the FDA. In some embodiments, an aluminum adjuvant is an aluminum phosphate adjuvant approved for administration to humans by the FDA.

The term "aluminum hydroxide adjuvant" as used herein refers to the aluminum hydroxide adjuvant that includes aluminum hydroxide and is currently used in human vaccines (e.g. marketed and/or approved human vaccines, such as FDA approved human vaccines). In some embodiments, "aluminum hydroxide adjuvant" as used herein refers to the aluminum hydroxide adjuvant that is currently used in human vaccines (e.g. marketed and/or approved human vaccines, such as FDA approved human vaccines) and is used in accordance with the use of that term in Hem S. L., Vaccine 23(2007) 4985-4986. In some embodiments, an aluminum hydroxide adjuvant includes CAS no. 21645-51-2. In some embodiments, an aluminum hydroxide adjuvant is aluminum hydroxide gel. In some embodiments, an aluminum hydroxide adjuvant is aluminum hydroxide gel in the form of a white gelatinous precipitate. In some embodiments, an aluminum hydroxide adjuvant includes aluminum hydroxide and does not include magnesium hydroxide. In some embodiments, an aluminum hydroxide adjuvant is Alhydrogel®. In some embodiments, an aluminum hydroxide adjuvant includes crystalline aluminum hydroxide and not amorphous aluminum hydroxide. In some embodiments, an aluminum hydroxide adjuvant includes crystalline aluminum and not amorphous aluminum. In some embodiments, an aluminum hydroxide adjuvant includes crystalline aluminum oxyhydroxide. In some embodiments, an aluminum hydroxide is crystalline aluminum oxyhydroxide. In some embodiments, an aluminum hydroxide adjuvant includes aluminum oxyhydroxide and not aluminum hydroxycarbonate. In some embodiments, an aluminum hydroxide adjuvant is aluminum oxyhydroxide and not aluminum hydroxycarbonate. In some embodiments, an aluminum hydroxide adjuvant does not include amorphous aluminum hydroxide in which some hydroxyls are replaced by sulfate anions. In some embodiments, aluminum hydroxide adjuvant includes aluminum oxyhydroxide in a Boehmite-like pattern. In some embodiments of an aluminum hydroxide adjuvant described above, the description is of the aluminum hydroxide adjuvant prior to inclusion in a vaccine.

The term "aluminum phosphate adjuvant" as used herein refers to the aluminum phosphate adjuvant that includes aluminum phosphate and is currently used in human vaccines (e.g. marketed and/or approved human vaccines, such as FDA approved human vaccines). In some embodiments, "aluminum phosphate adjuvant" as used herein refers to the aluminum phosphate adjuvant that is currently used in human vaccines (e.g. marketed and/or approved human vaccines, such as FDA approved human vaccines) and is used in accordance with the use of that term in Hem S. L., Vaccine 23(2007) 4985-4986. In some embodiments, an aluminum phosphate adjuvant includes CAS no. 7784-30-7. In some embodiments, an aluminum phosphate adjuvant is aluminum phosphate gel. In some embodiments, an aluminum phosphate adjuvant is aluminum phosphate gel in the form of a white gelatinous precipitate. In some embodiments, an aluminum phosphate adjuvant is Adju-Phos™. In some embodiments, an aluminum phosphate adjuvant is Adjuphos™. In some embodiments, an aluminum phosphate adjuvant includes amorphous aluminum hydroxyphosphate. In some embodiments of an aluminum phosphate adjuvant described above, the description is of the aluminum phosphate adjuvant prior to inclusion in a vaccine.

The terms "bind", "bound", "binding", and other verb forms thereof are used in accordance with their plain ordinary meaning within Enzymology and Biochemistry and refer to the formation of one or more interactions or contacts between two compositions that may optionally interact. Binding may be intermolecular or intramolecular.

The term "potassium aluminum sulfate adjuvant" refers to an adjuvant that includes potassium aluminum sulfate. The term "aluminum sulfate adjuvant" refers to an adjuvant that includes aluminum sulfate.

The term "vaccine" is used according to its plain ordinary meaning within medicine and Immunology and refers to a composition including an antigenic component (e.g. antigenic protein) for administration to a subject (e.g. human), which elicits an immune response to the antigenic component (e.g. antigentic protein). In some embodiments a vaccine is a therapeutic. In some embodiments, a vaccine is prophylactic. In some embodiments a vaccine includes one or more adjuvants (e.g. aluminum adjuvant). A liquid vaccine is a vaccine in liquid form, which may be for example a solution, suspension, emulsion, or dispersion or the antigenic component (e.g. antigenic protein) of the vaccine and may optionally include other components. A dry vaccine is a vaccine comprising 5% or less of water.

A vaccine is a preparation employed to improve immunity to a particular disease. Vaccines include an agent, which is used to induce a response from the immune system of the subject. Various agents that are typically used in a vaccine include, but are not limited to: killed, but previously virulent, micro-organisms; live, attenuated microorganisms; inactivated toxic compounds that are produced by microorganism that cause an illness; protein subunits of microorganisms; and conjugates. Examples of vaccines that may be converted into a powder immunogenic composition according to the methods described herein include, but are not limited to: influenza vaccine, cholera vaccine, bubonic plague vaccine, polio vaccine, Hepatitis A vaccine, rabies vaccine, yellow fever vaccine, measles vaccine, rubella vaccine, mumps vaccine, typhoid vaccine, tuberculosis vaccine, tetanus vaccine, diphtheria vaccine, diphtheria-tetanus-pertussis vaccine, Hepatitis B vaccine, human papillomavirus (HPV) vaccine, Pneumococcal conjugate vaccines, influenza vaccine, botulism vaccine, polio vaccine, and anthrax vaccines.

The term "prime-boost" or "prime boost" as applied to a methodology of administering vaccines is used according to its plain ordinary meaning in Virology and Immunology and refers to a method of vaccine administration in which a first dose of a vaccine or vaccine component is administered to a subject or patient to begin the administration (prime) and at a later time (e.g. hours, days, weeks, months later) a second vaccine is administered to the same patient or subject (boost). The first and second vaccines may be the same or different but are intended to both elicit an immune response useful in treating or preventing the same disease or condition. In some embodiments the prime is one or more viral proteins or portions thereof and the boost is one or more viral proteins or portions thereof.

The term "associated" or "associated with" as used herein to describe a disease (e.g. a virus associated disease or bacteria associated disease) means that the disease is caused by, or a symptom of the disease is caused by, what is described as disease associated or what is described as associated with the disease. As used herein, what is described as being associated with a disease, if a causative agent, could be a target for treatment of the disease.

The term "vaccinate", or additional verb forms thereof, refers to administering a vaccine to a subject (e.g. human) and eliciting an antigen specific immune response, wherein the antigen (e.g. antigenic protein) is included in the vaccine. The term "vaccinate" may also refer to eliciting an antigen specific immune response against an administered antigen (e.g. antigenic protein). In some embodiments, vaccinate is to provide prophylaxis against a disease or infectious agent. The term "portion" refers to a subset of a whole, which may also be the whole. In some embodiments, a portion is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. In some embodiments, a portion is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. Unless indicated otherwise, the term "about" in the context of a numeric value indicates the nominal value 10% of the nominal value. In some embodiments, "about" may be the nominal value.

III. Compositions

In an aspect is provided a dry vaccine including an antigenic protein and an aluminum adjuvant, wherein at least 75% of the antigenic protein is adsorbed to the aluminum adjuvant.

In embodiments, at least 60% of the antigenic protein is not denatured. In embodiments, at least 70% of the antigenic protein is not denatured. In embodiments, at least 80% of the antigenic protein is not denatured. In embodiments, at least 90% of the antigenic protein is not denatured. In embodiments, at least 95% of the antigenic protein is not denatured. In embodiments, at least 60% of the antigenic protein is in a conformationally native state. In embodiments, at least 70% of the antigenic protein is in a conformationally native state. In embodiments, at least 80% of the antigenic protein is in a conformationally native state. In embodiments, at least 90% of the antigenic protein is in a conformationally native state. In embodiments, at least 95% of the antigenic protein is in a conformationally native state. A "conformationally native state" is a folded conformation corresponding to an operative or functional protein. A "denatured" protein is a protein having a conformation differing from the folded active or functional conformation of the protein, wherein the denatured protein has a reduced level of activity or function. In embodiments, the antigenic protein is an unconjugated antigenic protein. In embodiments, the antigenic protein is an antigenic protein sugar (saccharide) conjugate. In embodiments, the sugar (saccharide) is a monosaccharide. In embodiments, the sugar (saccharide) is a disaccharide. In embodiments, the sugar (saccharide) is a polysaccharide.

In embodiments, the aluminum adjuvant includes aluminum hydroxide. In embodiments, the aluminum adjuvant includes aluminum phosphate. In embodiments, the aluminum adjuvant includes potassium aluminum sulfate. In embodiments, the aluminum adjuvant is aluminum hydroxide. In embodiments, the aluminum adjuvant is aluminum phosphate. In embodiments, the aluminum adjuvant is potassium aluminum sulfate. In embodiments, the aluminum adjuvant is aluminum sulfate. In embodiments, the dry vaccine includes between 0.5 and 5% (wt/wt) of the aluminum adjuvant. In embodiments, the dry vaccine includes between 0.5 and 4% (wt/wt) of the aluminum adjuvant. In embodiments, the dry vaccine includes between 0.5 and 3% (wt/wt) of the aluminum adjuvant. In embodiments, the dry vaccine includes between 0.5 and 2% (wt/wt) of the aluminum adjuvant. In embodiments, the dry vaccine includes between 0.75 and 2% (wt/wt) of the aluminum adjuvant. In embodiments, the dry vaccine includes between 1 and 2% (wt/wt) of the aluminum adjuvant. In embodiments, the dry vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes at least 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes less than 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes between 0.08 and 1% (wt/wt) of the aluminum adjuvant.

In embodiments, the dry vaccine includes less than 5% water. In embodiments, the dry vaccine includes less than 4% water. In embodiments, the dry vaccine includes less than 3% water. In embodiments, the dry vaccine includes less than 2% water. In embodiments, the dry vaccine includes less than 1% water. In embodiments, the dry vaccine includes less than 5% water (wt/wt). In embodiments, the dry vaccine includes less than 4% water (wt/wt). In embodiments, the dry vaccine includes less than 3% water (wt/wt). In embodiments, the dry vaccine includes less than 2% water (wt/wt). In embodiments, the dry vaccine includes less than 1% water (wt/wt). In embodiments, the dry vaccine includes about 5% water. In embodiments, the dry vaccine includes about 4% water. In embodiments, the dry vaccine includes about 3% water. In embodiments, the dry vaccine includes about 2% water. In embodiments, the dry vaccine includes about 1% water. In embodiments, the dry vaccine includes about 5% water (wt/wt). In embodiments, the dry vaccine includes about 4% water (wt/wt). In embodiments, the dry vaccine includes about 3% water (wt/wt). In embodiments, the dry vaccine includes about 2% water (wt/wt). In embodiments, the dry vaccine includes about 1% water (wt/wt). In embodiments, the dry vaccine includes less than 5% water (v/v). In embodiments, the dry vaccine includes less than 4% water (v/v). In embodiments, the dry vaccine includes less than 3% water (v/v). In embodiments, the dry vaccine includes less than 2% water (v/v). In embodiments, the dry vaccine includes less than 1% water (v/v). In embodiments, the dry vaccine includes about 5% water (v/v). In embodiments, the dry vaccine includes about 4% water (v/v). In embodiments, the dry vaccine includes about 3% water (v/v). In embodiments, the dry vaccine includes about 2% water (v/v). In embodiments, the dry vaccine includes about 1% water (v/v).

In embodiments, at least 75% of the antigenic protein is adsorbed to the aluminum adjuvant. In embodiments, at least 80% of the antigenic protein is adsorbed to the aluminum adjuvant. In embodiments, at least 85% of the antigenic protein is adsorbed to the aluminum adjuvant. In embodiments, at least 90% of the antigenic protein is adsorbed to the aluminum adjuvant. In embodiments, at least 92% of the antigenic protein is adsorbed to the aluminum adjuvant. In embodiments, at least 95% of the antigenic protein is adsorbed to the aluminum adjuvant. In embodiments, at least 98% of the antigenic protein is adsorbed to the aluminum adjuvant. In embodiments, at least 99% of the antigenic protein is adsorbed to the aluminum adjuvant. In embodiments, about 75% of the antigenic protein is adsorbed to the aluminum adjuvant. In embodiments, about 80% of the antigenic protein is adsorbed to the aluminum adjuvant. In embodiments, about 85% of the antigenic protein is adsorbed to the aluminum adjuvant. In embodiments, about 90% of the antigenic protein is adsorbed to the aluminum adjuvant. In embodiments, about 92% of the antigenic protein is adsorbed to the aluminum adjuvant. In embodiments, about 95% of the antigenic protein is adsorbed to the aluminum adjuvant. In embodiments, about 98% of the antigenic protein is adsorbed to the aluminum adjuvant. In embodiments, about 99% of the antigenic protein is adsorbed to the aluminum adjuvant.

In embodiments, the dry vaccine includes an excipient. In embodiments, the dry vaccine includes a plurality of different excipients. In embodiments, the excipient is a salt, sugar (saccharide), buffer, detergent, polymer, amino acid, or preservative. In embodiments, the excipient is disodium edetate, sodium chloride, sodium citrate, sodium succinate, sodium hydroxide, sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benzyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxyethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminophenyl-p-anisate, monosodium glutamate, beta-propiolactone, acetate, citrate, glutamate, glycinate, histidine, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer. In embodiments, the excipient is trehalose. In embodiments, the dry vaccine includes less than 5% wt/wt of the excipient. In embodiments, the dry vaccine includes less than 4% wt/wt of the excipient. In embodiments, the dry vaccine includes less than 3% wt/wt of the excipient. In embodiments, the dry vaccine includes less than 2% wt/wt of the excipient. In embodiments, the dry vaccine includes less than 1% wt/wt of the excipient. In embodiments, the dry vaccine includes less than 0.5% wt/wt of the excipient. In embodiments, the dry vaccine includes about 5% wt/wt of the excipient. In embodiments, the dry vaccine includes about 4% wt/wt of the excipient. In embodiments, the dry vaccine includes about 3% wt/wt of the excipient. In embodiments, the dry vaccine includes about 2% wt/wt of the excipient. In embodiments, the dry vaccine includes about 1% wt/wt of the excipient. In embodiments, the dry vaccine includes about 0.5% wt/wt of the excipient.

In embodiments, the dry vaccine includes particles, wherein the particles include the antigenic protein adsorbed to the aluminum adjuvant. In embodiments, the dry vaccine is prepared from a liquid vaccine.

In an embodiment, a powder (e.g. dry) vaccine, which retains its efficacy, may be made from a vaccine composition. The method includes obtaining a liquid (e.g. aqueous) vaccine composition. The vaccine composition includes an agent that resembles a disease-causing microorganism or a compound associated with the disease-causing microorganism (e.g. antigenic protein). The vaccine composition also includes an adjuvant (e.g. aluminum adjuvant). The vaccine composition is frozen to obtain a frozen vaccine composition (e.g. vaccine thin film). Water is removed from the frozen vaccine composition to form a powder (e.g. dry) vaccine that includes the agent or compound (e.g. antigenic protein) and the adjuvant (e.g. aluminum adjuvant).

A cryoprotectant may be added to the vaccine composition to protect the organisms or agents present in the composition (either live or dead) from damage during the freezing process. Examples of cryoprotectants include dimethyl sulfoxide, glycerol, monosaccharides, and polysaccharides (e.g. trehalose). A cryoprotectant may be present in amounts up to about 5% by weight.

Additionally, the solid form of the vaccine is expected to be advantageous over vaccine dispersion (i.e., suspension) for stockpiling vaccines that are critical to national security and public health. For example, botulism is a life-threatening disease caused by botulinum neurotoxins (BoNTs), which are produced by one of the seven structurally similar *Clostridium botulinum* serotypes, designated A to G. Each of the toxins is immunologically distinct, except that serotypes C and D share significant cross-homology. BoNTs are the most poisonous substances known in nature. A single gram of crystalline toxin, evenly dispersed and inhaled, would kill more than one million people. Previously, an investigational pentavalent botulism toxoid (PBT) vaccine aiming to protect against BoNT serotypes A-E had been available. However, as of November 2011, the PBT vaccine has been discontinued by the Centers for Disease Control and Prevention (CDC), based on "an assessment of the available data, which indicate a decline in immunogenicity of some of the toxin serotypes". Since the investigative PBT vaccine was the only botulism vaccine available in the U.S., discontinuation of it has significant national security implications.

In another embodiment, an aqueous vaccine composition may be composed of an agent and an aluminum adjuvant that form particles having a particle size of less than about 200 nm (e.g. less than 10, 20, 30, 40, 50, 60, 70, 80, 90, 100, 110, 120, 130, 140, 150, 160, 170, 180, 190, 200 nm). In some embodiments, aluminum hydroxide or aluminum phosphate particles having a diameter of less than 200 nm (e.g. less than 10, 20, 30, 40, 50, 60, 70, 80, 90, 100, 110, 120, 130, 140, 150, 160, 170, 180, 190, 200 nm) may be used as adjuvants in a vaccine composition. The vaccine composition may be formed by mixing the agent of the vaccine with the aluminum adjuvant particles in water. The aqueous vaccine composition may be used to vaccinate a subject against the disease related to the agent. In some embodiments, the aqueous vaccine composition can be converted to a vaccine powder, as described above, for storage, for use as an inhalant, or use in other delivery modes.

In embodiments, a dry vaccine is the dry vaccine described herein, including in embodiments, examples, tables, figures, and claims. In embodiments, a dry vaccine is a dry vaccine made by a method described herein, including in aspects, embodiments, examples, tables, figures, and claims. Provided herein is a reconstituted liquid vaccine comprising a dry vaccine as described herein (including in an aspect, embodiment, example, table, figure, or claim) or a dry vaccine prepared using a method as described herein (including in an aspect, embodiment, example, table, figure, or claim) and a solvent (e.g. water, buffer, solution, liquid including an excipient).

Provided in another aspect is a pharmaceutical composition including a pharmaceutically acceptable excipient and any of the compositions (e.g. vaccines) described herein (including embodiment).

The compositions described herein (including embodiments and examples) can be administered alone or can be coadministered to the patient. Coadministration is meant to include simultaneous or sequential administration of the compositions individually or in combination (more than one composition). Thus, the preparations can also be combined, when desired, with other active substances (e.g. to reduce metabolic degradation, increase immune response (e.g. adjuvants)). An example of coadministration of vaccine compositions is a prime-boost method of administration.

Pharmaceutical compositions provided by the present embodiments include compositions wherein the active ingredient (e.g. compositions described herein, including embodiments) is contained in a therapeutically or prophylactically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., prevent infection, and/or reducing, eliminating, or slowing the progression of disease symptoms. Determination of a therapeutically or prophylactically effective amount of a composition of the embodiments is well within the capabilities of those skilled in the art, especially in light of the detailed disclosure herein.

IV. Methods

In an aspect is provided a method for preparing a vaccine thin film including: applying a liquid vaccine to a freezing surface; allowing the liquid vaccine to disperse and freeze on the freezing surface thereby forming a vaccine thin film. The liquid vaccine includes aluminum (e.g. aluminum adjuvant).

In embodiments, the aluminum adjuvant includes aluminum hydroxide. In embodiments, the aluminum adjuvant includes aluminum phosphate. In embodiments, the aluminum adjuvant includes potassium aluminum sulfate. In embodiments, the aluminum adjuvant is aluminum hydroxide. In embodiments, the aluminum adjuvant is aluminum phosphate. In embodiments, the aluminum adjuvant is potassium aluminum sulfate. In embodiments, the aluminum adjuvant includes aluminum sulfate. In embodiments, the aluminum adjuvant is aluminum sulfate. In embodiments, the liquid vaccine includes between 0.5 and 5% (wt/wt) of the aluminum adjuvant. In embodiments, the liquid vaccine includes between 0.5 and 4% (wt/wt) of the aluminum adjuvant. In embodiments, the liquid vaccine includes between 0.5 and 3% (wt/wt) of the aluminum adjuvant. In embodiments, the liquid vaccine includes between 0.5 and 2% (wt/wt) of the aluminum adjuvant. In embodiments, the liquid vaccine includes between 0.75 and 2% (wt/wt) of the aluminum adjuvant. In embodiments, the liquid vaccine includes between 1 and 2% (wt/wt) of the aluminum adjuvant. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes at least 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes less than 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes between 0.5 and 5% (wt/vol) of the aluminum adjuvant/liquid vaccine. In embodiments, the liquid vaccine includes between 0.5 and 4% (wt/vol) of the aluminum adjuvant/liquid vaccine. In embodiments, the liquid vaccine includes between 0.5 and 3% (wt/vol) of the aluminum adjuvant/liquid vaccine. In embodiments, the liquid vaccine includes between 0.5 and 2% (wt/vol) of the aluminum adjuvant/liquid vaccine. In embodiments, the liquid vaccine includes between 0.75 and 2% (wt/vol) of the aluminum adjuvant/liquid vaccine. In embodiments, the liquid vaccine includes between 1 and 2% (wt/vol) of the aluminum adjuvant/liquid vaccine. In embodiments, the liquid vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes at least 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes less than 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes between 0.08 and 1% (wt/vol) of the aluminum adjuvant/liquid vaccine. In embodiments, the liquid vaccine includes between about 0.5 and about 5% (wt/wt) of the aluminum adjuvant. In embodiments, the liquid vaccine includes between about 0.5 and about 4% (wt/wt) of the aluminum adjuvant. In embodiments, the liquid vaccine includes between about 0.5 and about 3% (wt/wt) of the aluminum adjuvant. In embodiments, the liquid vaccine includes between about 0.5 and about 2% (wt/wt) of the aluminum adjuvant. In embodiments, the liquid vaccine includes between about 0.75 and about 2% (wt/wt) of the aluminum adjuvant. In embodiments, the liquid vaccine includes between about 1 and about 2% (wt/wt) of the aluminum adjuvant. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes at least about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes less than about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the liquid vaccine includes between about 0.5 and about 5% (wt/vol) of the aluminum adjuvant/liquid vaccine. In embodiments, the liquid vaccine includes between about 0.5 and about 4% (wt/vol) of the aluminum adjuvant/liquid vaccine. In embodiments, the liquid vaccine includes between about 0.5 and about 3% (wt/vol) of the aluminum adjuvant/liquid vaccine. In embodiments, the liquid vaccine includes between about 0.5 and about 2% (wt/vol) of the aluminum adjuvant/liquid vaccine. In embodiments, the liquid vaccine includes between about 0.75 and about 2% (wt/vol) of the aluminum adjuvant/liquid vaccine. In embodiments, the liquid vaccine includes between about 1 and about 2% (wt/vol) of the aluminum adjuvant/liquid vaccine. In embodiments, the liquid vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes at least about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes less than about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes about 0.08, 0.09, 0.1, 0.2, 0.3, 0.4, 0.5, 0.6, 0.7, 0.8, 0.9, 1, 2, 3, 4, 5, 6, 7, 8, 9, or 10% (wt/vol) of the aluminum adjuvant/liquid vaccine. In embodiments, the liquid vaccine includes between about 0.08 and about 1% (wt/vol) of the aluminum adjuvant/liquid vaccine.

In embodiments, the liquid vaccine includes a ratio of antigenic protein to aluminum adjuvant (wt/wt) of about 1:10. In embodiments, the liquid vaccine includes a ratio of antigenic protein to aluminum adjuvant (wt/wt) of about 1:9. In embodiments, the liquid vaccine includes a ratio of antigenic protein to aluminum adjuvant (wt/wt) of about 1:8. In embodiments, the liquid vaccine includes a ratio of antigenic protein to aluminum adjuvant (wt/wt) of about 1:7. In embodiments, the liquid vaccine includes a ratio of antigenic protein to aluminum adjuvant (wt/wt) of about 1:6. In embodiments, the liquid vaccine includes a ratio of antigenic protein to aluminum adjuvant (wt/wt) of about 1:5. In embodiments, the liquid vaccine includes a ratio of antigenic protein to aluminum adjuvant (wt/wt) of about 1:4. In embodiments, the liquid vaccine includes a ratio of antigenic protein to aluminum adjuvant (wt/wt) of about 1:3. In embodiments, the liquid vaccine includes a ratio of antigenic protein to aluminum adjuvant (wt/wt) of about 1:2. In embodiments, the liquid vaccine includes a ratio of antigenic protein to aluminum adjuvant (wt/wt) of about 1:1. In embodiments, the liquid vaccine includes a ratio of antigenic protein to aluminum adjuvant (wt/wt) of less than 1:10. In embodiments, the liquid vaccine includes a ratio of antigenic protein to aluminum adjuvant (wt/wt) of 1:10. In embodiments, the liquid vaccine includes a ratio of antigenic protein to aluminum adjuvant (wt/wt) of 1:9. In embodiments, the liquid vaccine includes a ratio of antigenic protein to aluminum adjuvant (wt/wt) of 1:8. In embodiments, the liquid vaccine includes a ratio of antigenic protein to aluminum adjuvant (wt/wt) of 1:7. In embodiments, the liquid vaccine includes a ratio of antigenic protein to aluminum adjuvant (wt/wt) of 1:6. In embodiments, the liquid vaccine includes a ratio of antigenic protein to aluminum adjuvant (wt/wt) of 1:5. In embodiments, the liquid vaccine includes a ratio of antigenic protein to aluminum adjuvant (wt/wt) of 1:4. In embodiments, the liquid vaccine includes a ratio of antigenic protein to aluminum adjuvant (wt/wt) of 1:3. In embodiments, the liquid vaccine includes a ratio of antigenic protein to aluminum adjuvant (wt/wt) of 1:2. In embodiments, the liquid vaccine includes a ratio of antigenic protein to aluminum adjuvant (wt/wt) of 1:1.

In embodiments, the liquid vaccine includes an excipient. In embodiments, the liquid vaccine includes a plurality of different excipients. In embodiments, the excipient is a salt, sugar (saccharide), buffer, detergent, polymer, amino acid, or preservative. In embodiments, the excipient is disodium edetate, sodium chloride, sodium citrate, sodium succinate, sodium hydroxide, Sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benzyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminophenyl-p-anisate, monosodium glutamate, beta-propiolactone, acetate, citrate, glutamate, glycinate, histidine, Lactate, Maleate, phosphate, succinate, tartarate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer. In embodiments, the excipient is trehalose. In embodiments, the liquid vaccine includes less than 5% wt/vol of the excipient/liquid vaccine. In embodiments, the liquid vaccine includes less than 4% wt/vol of the excipient/liquid vaccine. In embodiments, the liquid vaccine includes less than 3% wt/vol of the excipient/liquid vaccine. In embodiments, the liquid vaccine includes less than 2% wt/vol of the excipient/liquid vaccine. In embodiments, the liquid vaccine includes less than 1% wt/vol of the excipient/liquid vaccine. In embodiments, the liquid vaccine includes less than 0.5% wt/vol of the excipient/liquid vaccine. In embodiments, the liquid vaccine includes about 5% wt/vol of the excipient/liquid vaccine. In embodiments, the liquid vaccine includes about 4% wt/vol of the excipient/liquid vaccine. In embodiments, the liquid vaccine includes about 3% wt/vol of the excipient/liquid vaccine. In embodiments, the liquid vaccine includes about 2% wt/vol of the excipient/liquid vaccine. In embodiments, the liquid vaccine includes about 1% wt/vol of the excipient/liquid vaccine. In embodiments, the liquid vaccine includes about 0.5% wt/vol of the excipient/liquid vaccine. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% (wt/vol) of the excipient/liquid vaccine. In embodiments, the liquid vaccine includes 0.1, 0.2, 0.3, 0.4, 0.5, 0.6, 0.7, 0.8, 0.9, 1, 2, 3, 4, 5, 6, 7, 8, 9, or 10% (wt/vol) of the excipient/liquid vaccine. In embodiments, the liquid vaccine includes less than 5% of the excipient. In embodiments, the liquid vaccine includes less than 4% of the excipient. In embodiments, the liquid vaccine includes less than 3% of the excipient. In embodiments, the liquid vaccine includes less than 2% of the excipient. In embodiments, the liquid vaccine includes less than 1% of the excipient. In embodiments, the liquid vaccine includes less than 0.5% of the excipient. In embodiments, the liquid vaccine includes about 5% of the excipient. In embodiments, the liquid vaccine includes about 4% of the excipient. In embodiments, the liquid vaccine includes about 3% of the excipient. In embodiments, the liquid vaccine includes about 2% of the excipient. In embodiments, the liquid vaccine includes about 1% of the excipient. In embodiments, the liquid vaccine includes about 0.5% of the excipient. In embodiments, the liquid vaccine includes about 0.1, 0.2, 0.3, 0.4, 0.5, 0.6, 0.7, 0.8, 0.9, 1, 2, 3, 4, 5, 6, 7, 8, 9, or 10% of the excipient. In embodiments, the liquid vaccine includes 0.1, 0.2, 0.3, 0.4, 0.5, 0.6, 0.7, 0.8, 0.9, 1, 2, 3, 4, 5, 6, 7, 8, 9, or 10% of the excipient.

In embodiments, the applying includes spraying or dripping droplets of the liquid vaccine. In embodiments, the vapor-liquid interface of the droplets is less than 500 cm-1 area/volume. In embodiments, the vapor-liquid interface of the droplets is less than 400 cm-1 area/volume. In embodiments, the vapor-liquid interface of the droplets is less than 300 cm-1 area/volume. In embodiments, the vapor-liquid interface of the droplets is less than 200 cm-1 area/volume. In embodiments, the vapor-liquid interface of the droplets is less than 100 cm-1 area/volume. In embodiments, the vapor-liquid interface of the droplets is less than 50 cm-1 area/volume. In embodiments, the vapor-liquid interface of the droplets is less than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 cm-1 area/volume.

In embodiments, the method further includes contacting the droplets with a freezing surface having a temperature below the freezing temperature of the liquid vaccine (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 degrees Celsius below the freezing temperature). In embodiments, the method further includes contacting the droplets with a freezing surface having a temperature differential of at least 30° C. between the droplets and the surface. In embodiments, the temperature differential is at least 40° C. between the droplets and the surface. In embodiments, the temperature differential is at least 50° C. between the droplets and the surface. In embodiments, the temperature differential is at least 60° C. between the droplets and the surface. In embodiments, the temperature differential is at least 70° C. between the droplets and the surface. In embodiments, the temperature differential is at least 80° C. between the droplets and the surface. In embodiments, the temperature differential is at least 90° C. between the droplets and the surface. In embodiments, the temperature differential between the droplets and the surface is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 degrees Celsius.

In embodiments, the vaccine thin film has a thickness of less than 500 micrometers. In embodiments, the vaccine thin film has a thickness of less than 400 micrometers. In embodiments, the vaccine thin film has a thickness of less than 300 micrometers. In embodiments, the vaccine thin film has a thickness of less than 200 micrometers. In embodiments, the vaccine thin film has a thickness of less than 100 micrometers. In embodiments, the vaccine thin film has a thickness of less than 50 micrometers. In embodiments, the vaccine thin film has a thickness of less than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micrometers. In embodiments, the vaccine thin film has a thickness of about 500 micrometers. In embodiments, the vaccine thin film has a thickness of about 400 micrometers. In embodiments, the vaccine thin film has a thickness of about 300 micrometers. In embodiments, the vaccine thin film has a thickness of about 200 micrometers. In embodiments, the vaccine thin film has a thickness of about 100 micrometers. In embodiments, the vaccine thin film has a thickness of about 50 micrometers. In embodiments, the vaccine thin film has a thickness of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micrometers.

In embodiments, the vaccine thin film has a surface area to volume ratio of between 25 and 500 cm$^{-1}$. In embodiments, the vaccine thin film has a surface area to volume ratio of between 25 and 400 cm$^{-1}$. In embodiments, the vaccine thin film has a surface area to volume ratio of between 25 and 300 cm$^{-1}$. In embodiments, the vaccine thin film has a surface area to volume ratio of between 25 and 200 cm$^{-1}$. In embodiments, the vaccine thin film has a surface area to volume ratio of between 25 and 100 cm$^{-1}$. In embodiments, the vaccine thin film has a surface area to volume ratio of between 100 and 500 cm$^{-1}$. In embodiments, the vaccine thin film has a surface area to volume ratio of between 200 and 500 cm$^{-1}$. In embodiments, the vaccine thin film has a surface area to volume ratio of between 300 and 500 cm$^{-1}$. In embodiments, the vaccine thin film has a surface area to volume ratio of between 400 and 500 cm$^{-1}$. In embodiments, the vaccine thin film has a surface area to volume ratio of between 100 and 400 cm$^{-1}$. In embodiments, the vaccine thin film has a surface area to volume ratio of between 200 and 300 cm$^{-1}$. In embodiments, the vaccine thin film has a surface area to volume ratio of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 cm$^{-1}$. In embodiments, the vaccine thin film has a surface area to volume ratio of between about 25 and about 500 cm$^{-1}$. In embodiments, the vaccine thin film has a surface area to volume ratio of between about 25 and about 400 cm$^{-1}$. In embodiments, the vaccine thin film has a surface area to volume ratio of between about 25 and about 300 cm$^{-1}$. In embodiments, the vaccine thin film has a surface area to volume ratio of between about 25 and about 200 cm$^{-1}$. In embodiments, the vaccine thin film has a surface area to volume ratio of between about 25 and about 100 cm$^{-1}$. In embodiments, the vaccine thin film has a surface area to volume ratio of between about 100 and about 500 cm$^{-1}$. In embodiments, the vaccine thin film has a surface area to volume ratio of between about 200 and about 500 cm$^{-1}$. In embodiments, the vaccine thin film has a surface area to volume ratio of between about 300 and about 500 cm$^{-1}$. In embodiments, the vaccine thin film has a surface area to volume ratio of between about 400 and about 500 cm$^{-1}$. In embodiments, the vaccine thin film has a surface area to volume ratio of between about 100 and about 400 cm$^{-1}$. In embodiments, the vaccine thin film has a surface area to volume ratio of between about 200 and about 300 cm$^{-1}$.

In embodiments, the freezing rate of the droplets is between about 10 K/second and about $10^5$ K/second. In embodiments, the freezing rate of the droplets is between about 10 K/second and about $10^4$ K/second. In embodiments, the freezing rate of the droplets is between about 10 K/second and about $10^3$ K/second. In embodiments, the freezing rate of the droplets is between about $10^2$ K/second and about $10^3$ K/second. In embodiments, the freezing rate of the droplets is between about 50 K/second and about $5 \times 10^2$ K/second. In embodiments, the freezing rate of the droplets is between 10 K/second and $10^5$ K/second. In embodiments, the freezing rate of the droplets is between 10 K/second and $10^4$ K/second. In embodiments, the freezing rate of the droplets is between 10 K/second and $10^3$ K/second. In embodiments, the freezing rate of the droplets is between $10^2$ K/second and $10^3$ K/second. In embodiments, the freezing rate of the droplets is between 50 K/second and $5 \times 10^2$ K/second. In embodiments, the freezing rate of the droplets is about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 K/second. In embodiments, the freezing rate of the droplets is 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 K/second. In embodiments, each of the droplets freezes upon contact with the freezing surface in less than about 50, 75, 100, 125, 150, 175, 200, 250, 500, 1,000, or 2,000 milliseconds. In embodiments, each of the droplets freezes upon contact with the freezing surface in less than 50, 75, 100, 125, 150, 175, 200, 250, 500, 1,000, or 2,000 milliseconds.

In embodiments, the droplets have an average diameter between about 0.1 and about 5 mm, between about 20 and about 24 degrees Celsius. In embodiments, the droplets have an average diameter between about 2 and about 4 mm, between about 20 and about 24 degrees Celsius. In embodiments, the droplets have an average diameter between about 1 and about 4 mm, between about 20 and about 24 degrees Celsius. In embodiments, the droplets have an average diameter between about 2 and about 3 mm, between about 20 and about 24 degrees Celsius. In embodiments, the droplets have an average diameter between about 1 and about 3 mm, between about 20 and about 24 degrees Celsius. In embodiments, the droplets have an average diameter between about 1 and about 2 mm, between about 20 and about 24 degrees Celsius. In embodiments, the droplets have an average diameter between about 3 and about 4 mm, between about 20 and about 24 degrees Celsius. In embodiments, the droplets have an average diameter between 0.1 and 5 mm, between 20 and 24 degrees Celsius. In embodiments, the droplets have an average diameter between 2 and 4 mm, between 20 and 24 degrees Celsius. In embodiments, the droplets have an average diameter between 1 and 4 mm, between 20 and 24 degrees Celsius. In embodiments, the droplets have an average diameter between 2 and 3 mm, between 20 and 24 degrees Celsius. In embodiments, the droplets have an average diameter between 1 and 3 mm, between 20 and 24 degrees Celsius. In embodiments, the droplets have an average diameter between 1 and 2 mm, between 20 and 24 degrees Celsius. In embodiments, the droplets have an average diameter between 3 and 4 mm, between 20 and 24 degrees Celsius.

In embodiments, the step of spraying or dripping droplets is repeated to overlay one or more additional vaccine thin films on top of the vaccine thin film. In embodiments, the step of spraying or dripping droplets is repeated to overlay 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 additional vaccine thin films on top of the first vaccine thin film.

In embodiments, the method further includes removing the solvent (e.g. water or liquid) from the vaccine thin film to form a dry vaccine.

In embodiments, is a method of making a dry vaccine from a vaccine thin film (e.g. including a vaccine thin film made using a method as described herein), including removing the solvent (e.g. water or liquid) from the vaccine thin film to form a dry vaccine. In embodiments of the methods described herein, the dry vaccine is a dry vaccine as described herein, including in an aspect, embodiment, example, table, figure, or claim. In embodiments, a method of making a vaccine thin film or a method of making dry vaccine is used to make a dry vaccine as described herein, including in an aspect, embodiment, example, table, figure, or claim.

In embodiments, the removing of the solvent includes lyophilization. In embodiments, the removing of the solvent includes lyophilization at temperatures of 20 degrees Celsius or less. In embodiments, the removing of the solvent includes lyophilization at temperatures of 25 degrees Celsius or less. In embodiments, the solvent includes lyophilization at temperatures of 40 degrees Celsius or less. In embodiments, the removing of the solvent includes lyophilization at temperatures of 50 degrees Celsius or less. In embodiments, the removing of the solvent includes lyophilization at temperatures of about 20 degrees Celsius or less. In embodiments, the removing of the solvent includes lyophilization at temperatures of about 25 degrees Celsius or less. In embodiments, the solvent includes lyophilization at temperatures of about 40 degrees Celsius or less. In embodiments, the removing of the solvent includes lyophilization at temperatures of about 50 degrees Celsius or less.

In embodiments, the dry vaccine includes between about 0.5 and about 5% (wt/wt) of the aluminum adjuvant. In embodiments, the dry vaccine includes between about 0.5 and about 4% (wt/wt) of the aluminum adjuvant. In embodiments, the dry vaccine includes between about 0.5 and about 3% (wt/wt) of the aluminum adjuvant. In embodiments, the dry vaccine includes between about 0.5 and about 2% (wt/wt) of the aluminum adjuvant. In embodiments, the dry vaccine includes between about 0.75 and about 2% (wt/wt) of the aluminum adjuvant. In embodiments, the dry vaccine includes between about 1 and about 2% (wt/wt) of the aluminum adjuvant. In embodiments, the dry vaccine includes between 0.5 and 5% (wt/wt) of the aluminum adjuvant. In embodiments, the dry vaccine includes between 0.5 and 4% (wt/wt) of the aluminum adjuvant. In embodiments, the dry vaccine includes between 0.5 and 3% (wt/wt) of the aluminum adjuvant. In embodiments, the dry vaccine includes between 0.5 and 2% (wt/wt) of the aluminum adjuvant. In embodiments, the dry vaccine includes between 0.75 and 2% (wt/wt) of the aluminum adjuvant. In embodiments, the dry vaccine includes between 1 and 2% (wt/wt) of the aluminum adjuvant. In embodiments, the dry vaccine includes about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes at least 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes less than 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes at least about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes less than about 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant. In embodiments, the dry vaccine includes 0.1, 0.2, 0.3, 0.4, 0.5, 0.6, 0.7, 0.8, 0.9, 1, 2, 3, 4, 5, 6, 7, 8, 9, or 10% (wt/wt) of the aluminum adjuvant.

In embodiments, the method further includes solvating the dry vaccine thereby forming a reconstituted liquid vaccine. A reconstituted liquid vaccine may also be called a solvated dry vaccine.

In embodiments, is a method of making a reconstituted liquid vaccine from a dry vaccine (e.g. including a dry vaccine made using a method as described herein), including solvating a dry vaccine and thereby forming a reconstituted liquid vaccine. In embodiments of the methods described herein, the dry vaccine is a dry vaccine as described herein, including in an aspect, embodiment, example, table, figure, or claim. In embodiments, a method of making a vaccine thin film, a method of making a dry vaccine, or a method of reconstituting a liquid vaccine is used to make a reconstituted liquid vaccine as described herein, including in an aspect, embodiment, example, table, figure, or claim.

In embodiments, the immunogenicity of the reconstituted liquid vaccine is at least 60% the immunogenicity of the liquid vaccine (prior to forming the dry vaccine from the liquid vaccine). In embodiments, the immunogenicity of the reconstituted liquid vaccine is at least 70% the immunogenicity of the liquid vaccine (prior to forming the dry vaccine from the liquid vaccine). In embodiments, the immunogenicity of the reconstituted liquid vaccine is at least 80% the immunogenicity of the liquid vaccine (prior to forming the dry vaccine from the liquid vaccine). In embodiments, the immunogenicity of the reconstituted liquid vaccine is at least 90% the immunogenicity of the liquid vaccine (prior to forming the dry vaccine from the liquid vaccine). In embodiments, the immunogenicity of the reconstituted liquid vaccine is at least 95% the immunogenicity of the liquid vaccine (prior to forming the dry vaccine from the liquid vaccine). In embodiments, the immunogenicity of the reconstituted liquid vaccine is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% the immunogenicity of the liquid vaccine (prior to forming the dry vaccine from the liquid vaccine). In embodiments, the immunogenicity of the reconstituted liquid vaccine is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% the immunogenicity of the liquid vaccine (prior to forming the dry vaccine from the liquid vaccine).

In embodiments, the level of antigenic protein adsorbed to the aluminum adjuvant of the reconstituted liquid vaccine is at least 60% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 70% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 80% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 90% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 95% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 99% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the level of antigenic protein adsorbed to the aluminum adjuvant of the liquid vaccine (prior to forming the dry vaccine from the liquid vaccine). In embodiments, the level of antigenic protein adsorbed to the aluminum adjuvant of the reconstituted liquid vaccine is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the level of antigenic protein adsorbed to the aluminum adjuvant of the liquid vaccine (prior to forming the dry vaccine from the liquid vaccine).

In embodiments, the reconstituted liquid vaccine includes particles, wherein the particles include the antigenic protein adsorbed to the aluminum adjuvant. In embodiments, the particles have an average diameter of between about 10 nm and about 2 μm. In embodiments, the particles have an average diameter of between about 20 nm and about 2 μm. In embodiments, the particles have an average diameter of between about 50 nm and about 2 μm. In embodiments, the particles have an average diameter of between about 100 nm and about 2 μm. In embodiments, the particles have an average diameter of between about 200 nm and about 2 μm. In embodiments, the particles have an average diameter of between about 500 nm and about 2 μm. In embodiments, the particles have an average diameter of between about 1 μm and about 2 μm. In embodiments, the particles have an average diameter of between about 10 nm and about 1 μm. In embodiments, the particles have an average diameter of between about 10 nm and about 500 nm. In embodiments, the particles have an average diameter of between about 10 nm and about 200 nm. In embodiments, the particles have an average diameter of between about 10 nm and about 200 nm. In embodiments, the particles have an average diameter of between about 10 nm and about 100 nm. In embodiments, the particles have an average diameter of between about 10 nm and about 50 nm. In embodiments, the particles have an average diameter of between about 10 nm and about 20 nm. In embodiments, the particles have an average diameter of between about 20 nm and about 1 μm. In embodiments, the particles have an average diameter of between about 50 nm and about 500 nm. In embodiments, the particles have an average diameter of between about 100 nm and about 500 nm. In embodiments, the particles have an average diameter of between about 100 nm and about 200 nm. In embodiments, the reconstituted liquid vaccine includes particles, wherein the particles include the antigenic protein adsorbed to the aluminum adjuvant. In embodiments, the particles have an average diameter of between 10 nm and 2 μm. In embodiments, the particles have an average diameter of between 20 nm and 2 μm. In embodiments, the particles have an average diameter of between 50 nm and 2 μm. In embodiments, the particles have an average diameter of between 100 nm and 2 μm. In embodiments, the particles have an average diameter of between 200 nm and 2 μm. In embodiments, the particles have an average diameter of between 500 nm and 2 μm. In embodiments, the particles have an average diameter of between 1 μm and 2 μm. In embodiments, the particles have an average diameter of between 10 nm and 1 μm. In embodiments, the particles have an average diameter of between 10 nm and 500 nm. In embodiments, the particles have an average diameter of between 10 nm and 200 nm. In embodiments, the particles have an average diameter of between 10 nm and 200 nm. In embodiments, the particles have an average diameter of between 10 nm and 100 nm. In embodiments, the particles have an average diameter of between 10 nm and 50 nm. In embodiments, the particles have an average diameter of between 10 nm and 20 nm. In embodiments, the particles have an average diameter of between 20 nm and 1 μm. In embodiments, the particles have an average diameter of between 50 nm and 500 nm. In embodiments, the particles have an average diameter of between 100 nm and 500 nm. In embodiments, the particles have an average diameter of between 100 nm and 200 nm. In embodiments, the particles are non-crystalline. In embodiments, the particles are amorphous.

In embodiments, the particles have an average diameter of between about 1 μm and about 50 μm. In embodiments, the particles have an average diameter of between about 10 μm and about 50 μm. In embodiments, the particles have an average diameter of between about 20 μm and about 50 μm. In embodiments, the particles have an average diameter of between about 30 μm and about 50 μm. In embodiments, the particles have an average diameter of between about 40 μm and about 50 μm. In embodiments, the particles have an average diameter of between about 10 μm and about 40 μm.

In embodiments, the particles have an average diameter of between about 10 μm and about 30 μm. In embodiments, the particles have an average diameter of between about 10 μm and about 20 μm. In embodiments, the particles have an average diameter of between about 1 μm and about 10 μm. In embodiments, the particles have an average diameter of between 1 μm and 50 μm. In embodiments, the particles have an average diameter of between 10 μm and 50 μm. In embodiments, the particles have an average diameter of between 20 μm and 50 μm. In embodiments, the particles have an average diameter of between 30 μm and 50 μm. In embodiments, the particles have an average diameter of between 40 μm and 50 μm. In embodiments, the particles have an average diameter of between 10 μm and 40 μm. In embodiments, the particles have an average diameter of between 10 μm and 30 μm. In embodiments, the particles have an average diameter of between 10 μm and 20 μm. In embodiments, the particles have an average diameter of between 1 μm and 10 μm. In embodiments, the particles have an average diameter of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm. In embodiments, the particles have an average diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm.

In embodiments, the reconstituted liquid vaccine includes particles including antigenic protein adsorbed to the aluminum adjuvant of the same average diameter as the liquid vaccine (prior to forming the dry vaccine from the liquid vaccine) particles including antigenic protein adsorbed to the aluminum adjuvant. In embodiments, the reconstituted liquid vaccine includes particles including antigenic protein adsorbed to the aluminum adjuvant having an average diameter within 5% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 10% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 20% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 30% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% of the average diameter of particles including the antigenic protein adsorbed to the aluminum adjuvant in the liquid vaccine (prior to forming the dry vaccine from the liquid vaccine). In embodiments, the reconstituted liquid vaccine includes particles including antigenic protein adsorbed to the aluminum adjuvant having an average diameter within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% of the average diameter of particles including the antigenic protein adsorbed to the aluminum adjuvant in the liquid vaccine (prior to forming the dry vaccine from the liquid vaccine).

In embodiments, the solvating of the dry vaccine is at least one day after preparing the dry vaccine from the liquid vaccine (e.g. the dry vaccine is stored for at least one day). In embodiments, the solvating of the dry vaccine is at least two days after preparing the dry vaccine from the liquid vaccine (e.g. the dry vaccine is stored for at least two days). In embodiments, the solvating of the dry vaccine is at least three days after preparing the dry vaccine from the liquid vaccine (e.g. the dry vaccine is stored for at least three days). In embodiments, the solvating of the dry vaccine is at least one week after preparing the dry vaccine from the liquid vaccine (e.g. the dry vaccine is stored for at least one week). In embodiments, the solvating of the dry vaccine is at least two weeks after preparing the dry vaccine from the liquid vaccine (e.g. the dry vaccine is stored for at least two weeks). In embodiments, the solvating of the dry vaccine is at least one month after preparing the dry vaccine from the liquid vaccine (e.g. the dry vaccine is stored for at least one month). In embodiments, the solvating of the dry vaccine is at least two months after preparing the dry vaccine from the liquid vaccine (e.g. the dry vaccine is stored for at least two months). In embodiments, the solvating of the dry vaccine is at least three months after preparing the dry vaccine from the liquid vaccine (e.g. the dry vaccine is stored for at least three months). In embodiments, the solvating of the dry vaccine is at least six months after preparing the dry vaccine from the liquid vaccine (e.g. the dry vaccine is stored for at least six months). In embodiments, the solvating of the dry vaccine is at least one year after preparing the dry vaccine from the liquid vaccine (e.g. the dry vaccine is stored for at least one year). In embodiments, the solvating of the dry vaccine is at least two years after preparing the dry vaccine from the liquid vaccine (e.g. the dry vaccine is stored for at least two years). In embodiments, the solvating of the dry vaccine is at least three years after preparing the dry vaccine from the liquid vaccine (e.g. the dry vaccine is stored for at least three years). In embodiments, the solvating of the dry vaccine is at least five years after preparing the dry vaccine from the liquid vaccine (e.g. the dry vaccine is stored for at least five years). In embodiments, the solvating of the dry vaccine is at least ten years after preparing the dry vaccine from the liquid vaccine (e.g. the dry vaccine is stored for at least ten years).

In embodiments, prior to the solvating of the dry vaccine, the dry vaccine is stored at about 4 degrees Celsius for at least 99% of the time. In embodiments, prior to the solvating of the dry vaccine, the dry vaccine is stored at less than 4 degrees Celsius for at least 99% of the time. In embodiments, prior to the solvating of the dry vaccine, the dry vaccine is stored at less than 0 degrees Celsius for at least 99% of the time. In embodiments, prior to the solvating of the dry vaccine, the dry vaccine is stored at less than −20 degrees Celsius for at least 99% of the time. In embodiments, prior to the solvating of the dry vaccine, the dry vaccine is stored at about −20 degrees Celsius for at least 99% of the time. In embodiments, prior to the solvating of the dry vaccine, the dry vaccine is stored at less than −80 degrees Celsius for at least 99% of the time. In embodiments, prior to the solvating of the dry vaccine, the dry vaccine is stored at about −80 degrees Celsius for at least 99% of the time. In embodiments, prior to the solvating of the dry vaccine, the dry vaccine is stored at ambient temperatures (e.g. room temperature). In embodiments, prior to the solvating of the dry vaccine, the dry vaccine is stored at between 20 and 24 degrees Celsius for at least 99% of the time. In embodiments, prior to the solvating of the dry vaccine, the dry vaccine is stored at between 4 and 24 degrees Celsius for at least 99% of the time. In embodiments, prior to the solvating of the dry vaccine, the dry vaccine is stored at between 0 and 24 degrees Celsius for at least 99% of the time. In embodiments, prior to the solvating of the dry vaccine, the dry vaccine is stored at between 4 and 40 degrees Celsius for at least 99% of the time. In embodiments, prior to the solvating of the dry vaccine, the dry vaccine is stored at between 0 and 40 degrees Celsius for at least 99% of the time. In embodiments, prior to the solvating of the dry vaccine, the dry vaccine is stored at about 4 degrees Celsius for at least 90% of the time. In embodiments, prior to the solvating of the dry vaccine, the dry vaccine is stored at less than 4 degrees Celsius for at least 90% of the time. In embodiments, prior to the solvating of the dry vaccine, the dry vaccine is stored at less than 0 degrees Celsius for at least 90% of the time. In embodiments, prior to the solvating of the dry vaccine, the dry vaccine is stored at less than −20 degrees Celsius for at least 90% of the time. In embodiments, prior to the solvating of the dry vaccine, the dry vaccine is stored at between 20 and 24 degrees Celsius for at least 90% of the time. In embodiments, prior to the solvating of the dry vaccine, the dry vaccine is stored at between 4 and 24 degrees Celsius for at least 90% of the time. In embodiments, prior to the solvating of the dry vaccine, the dry vaccine is stored at between 0 and 24 degrees Celsius for at least 90% of the time. In embodiments, prior to the solvating of the dry vaccine, the dry vaccine is stored at between 4 and 40 degrees Celsius for at least 90% of the time. In embodiments, prior to the solvating of the dry vaccine, the dry vaccine is stored at between 0 and 40 degrees Celsius for at least 90% of the time.

In embodiments, upon solvating the dry vaccine the resulting reconstituted liquid vaccine remains homogeneous. As used in reference to the status of a reconstituted liquid vaccine, the term "homogenous" refers to a lack of a significant amount of aggregation and/or precipitation forming, such that the reconstituted liquid vaccine does not include solid matter that is not evenly dispersed (e.g. solid matter visible to the naked eye, solid matter that settles in the liquid, solid matter that was not apparent in a liquid vaccine prior to formation of the dry vaccine and reconstitution, precipitate that was not present in the liquid vaccine prior to formation of the dry vaccine). A homogenous reconstituted liquid sample may include particles of antigenic protein adsorbed to aluminum adjuvant (e.g. that are suspended or dispersed in the reconstituted liquid vaccine). In embodiments, upon solvating the dry vaccine the resulting reconstituted liquid vaccine remains homogeneous for at least one day. In embodiments, upon solvating the dry vaccine the resulting reconstituted liquid vaccine remains homogeneous for at least two days. In embodiments, upon solvating the dry vaccine the resulting reconstituted liquid vaccine remains homogeneous for at least three days. In embodiments, upon solvating the dry vaccine the resulting reconstituted liquid vaccine remains homogeneous for at least one week. In embodiments, upon solvating the dry vaccine the resulting reconstituted liquid vaccine remains homogeneous for at least two weeks. In embodiments, upon solvating the dry vaccine the resulting reconstituted liquid vaccine remains homogeneous for at least one month. In embodiments, upon solvating the dry vaccine the resulting reconstituted liquid vaccine remains homogeneous for at least three months. In embodiments, upon solvating the dry vaccine the resulting reconstituted liquid vaccine remains homogeneous for at least six months. In embodiments, upon solvating the dry vaccine the resulting reconstituted liquid vaccine remains homogeneous for at least one year. In embodiments, upon solvating the dry vaccine the resulting reconstituted liquid vaccine does not form a precipitate (e.g. solid matter visible to the naked eye, solid matter that settles in the liquid, solid matter that was not apparent in a liquid vaccine prior to formation of the dry vaccine and reconstitution, precipitate that was not present in the liquid vaccine prior to formation of the dry vaccine). In embodiments, upon solvating the dry vaccine the resulting reconstituted liquid vaccine does not form a precipitate for at least one day. In embodiments, upon solvating the dry vaccine the resulting reconstituted liquid vaccine does not form a precipitate for at least two days. In embodiments, upon solvating the dry vaccine the resulting reconstituted liquid vaccine does not form a precipitate for at least three days. In embodiments, upon solvating the dry vaccine the resulting reconstituted liquid vaccine does not form a precipitate for at least one week. In embodiments, upon solvating the dry vaccine the resulting reconstituted liquid vaccine does not form a precipitate for at least two weeks. In embodiments, upon solvating the dry vaccine the resulting reconstituted liquid vaccine does not form a precipitate for at least one month. In embodiments, upon solvating the dry vaccine the resulting reconstituted liquid vaccine does not form a precipitate for at least three months. In embodiments, upon solvating the dry vaccine the resulting reconstituted liquid vaccine does not form a precipitate for at least six months. In embodiments, upon solvating the dry vaccine the resulting reconstituted liquid vaccine does not form a precipitate for at least one year. In embodiments, the precipitate includes particles having an average diameter greater than 50 μm. In embodiments, the precipitate includes particles having an average diameter greater than 100 μm. In embodiments, the precipitate includes particles having an average diameter greater than 200 μm. In embodiments, the precipitate includes particles having an average diameter greater than 300 μm. In embodiments, the precipitate includes particles having an average diameter greater than 400 μm. In embodiments, the precipitate includes particles having an average diameter greater than 500 μm. In embodiments, the precipitate includes particles having an average diameter greater than 600 μm. In embodiments, the precipitate includes particles having an average diameter greater than 700 μm. In embodiments, the precipitate includes particles having an average diameter greater than 800 μm. In embodiments, the precipitate includes particles having an average diameter greater than 900 μm. In embodiments, the precipitate includes particles having an average diameter greater than 1000 μm. In embodiments, the precipitate includes particles having an average diameter greater than about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μm. In embodiments, the precipitate includes particles having an average diameter of about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate includes particles having an average diameter greater than 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate (that is not formed) includes particles having an average diameter of 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm. In embodiments, the precipitate (that is not formed) includes at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the total antigenic protein absorbed to an aluminum adjuvant in the reconstituted liquid vaccine. In embodiments, upon solvating the dry vaccine the resulting reconstituted liquid vaccine does not form a precipitate including more than about 1% of the total antigenic protein in the reconstituted liquid vaccine. In embodiments, upon solvating the dry vaccine the resulting reconstituted liquid vaccine does not form a precipitate including more than about 2% of the total antigenic protein in the reconstituted liquid vaccine. In embodiments, upon solvating the dry vaccine the resulting reconstituted liquid vaccine does not form a precipitate including more than about 3% of the total antigenic protein in the reconstituted liquid vaccine. In embodiments, upon solvating the dry vaccine the resulting reconstituted liquid vaccine does not form a precipitate including more than about 4% of the total antigenic protein in the reconstituted liquid vaccine. In embodiments, upon solvating the dry vaccine the resulting reconstituted liquid vaccine does not form a precipitate including more than about 5% of the total antigenic protein in the reconstituted liquid vaccine. In embodiments, upon solvating the dry vaccine the resulting reconstituted liquid vaccine does not form a precipitate including more than about 1, 2, 3, 4, 5, 6, 7, 8, 9, 10, 11, 12, 13, 14, 15, 16, 17, 18, 19, or 20% of the total antigenic protein in the reconstituted liquid vaccine. In embodiments the precipitate includes irreversible aggregates of antigenic protein and/or aluminum adjuvant.

In embodiments, the liquid vaccine includes a commercially available vaccine. In embodiments, the liquid vaccine is a commercially available vaccine. In embodiments, the liquid vaccine has received market approval from the US FDA or the corresponding authority in another country. In embodiments, the liquid vaccine is a vaccine for the treatment of diphtheria, tetanus, pertussis, influenza, pneumonia, otitis media, bacteremia, meningitis, hepatitis, cirrhosis, anthrax poisoning, botulism, rabies, warts, poliomyelitis, Japanese encephalitis, or cancer. In embodiments, the liquid vaccine is a vaccine for the treatment of infection by *Clostridium tetani, Clostridium botulinum, Streptococcus pneumonia*, Hepatitis A, Hepatitis B, *Haemophilus* influenza, *Corynebacterium diphtheria, Bordetella pertussis, Human papillomavirus, Bacillus anthracis*, Rabies virus, Japanese encephalitis virus, or Poliovirus. In embodiments, the liquid vaccine includes a commercially available vaccine and another component not included in the commercially available vaccine (e.g. an excipient (e.g. trehalose)).

In an aspect is provided a method of treating a disease in a patient in need of such treatment, the method including administering a therapeutically effective amount of a solvated dry vaccine as described herein (e.g. in an aspect, embodiment, example, table, figure, or claims) (e.g. a reconstituted liquid vaccine as described herein) to the patient.

In embodiments, the disease is diphtheria, tetanus, pertussis, influenza, pneumonia, otitis media, bacteremia, meningitis, hepatitis, cirrhosis, anthrax poisoning, rabies, warts, poliomyelitis, Japanese encephalitis, or cancer. In embodiments, the disease is caused by an infectious agent. In embodiments, the infectious agent is a bacterium. In embodiments, the infectious agent is a virus. In embodiments, the infectious agent is *Clostridium tetani, Clostridium botulinum, Streptococcus pneumonia*, Hepatitis A, Hepatitis B, *Haemophilus* influenza, *Corynebacterium diphtheria, Bordetella pertussis, Human papillomavirus, Bacillus anthracis*, Rabies virus, Japanese encephalitis virus, or Poliovirus.

In an aspect is provided a method of treating a disease in a patient in need of such treatment, the method including administering a therapeutically effective amount of dry vaccine as described herein (e.g. in an aspect, embodiment, example, table, figure, or claims) (e.g. a reconstituted liquid vaccine as described herein) to the patient.

In embodiments, the disease is diphtheria, tetanus, pertussis, influenza, pneumonia, otitis media, bacteremia, meningitis, hepatitis, cirrhosis, anthrax poisoning, botulism, rabies, warts, poliomyelitis, Japanese encephalitis, or cancer. In embodiments, the disease is caused by an infectious agent. In embodiments, the infectious agent is a bacterium. In embodiments, the infectious agent is a virus. In embodiments, the infectious agent is *Clostridium tetani, Clostridium botulinum, Streptococcus pneumonia*, Hepatitis A, Hepatitis B, *Haemophilus* influenza, *Corynebacterium diphtheria, Bordetella pertussis, Human papillomavirus, Bacillus anthracis*, Rabies virus, Japanese encephalitis virus, or Poliovirus.

In embodiments, the dry vaccine is administered by inhalation, intradermally, orally, or vaginally. In embodiments, the dry vaccine is administered through the nasal mucosa, bronchoalveolar mucosa, or gastrointestinal mucosa.

In embodiments, the method is a method described herein, including in an aspect, embodiment, example, table, figure, or claim. Provided herein is a method of preparing a dry vaccine including a method of preparing a vaccine thin film as described herein (including in an aspect, embodiment, example, table, figure, or claim) and a method of removing a solvent from a vaccine thin film as described herein (including in an aspect, embodiment, example, table, figure, or claim). Provided herein is a method of preparing a reconstituted dry vaccine including a method of preparing a dry vaccine as described herein (including in an aspect, embodiment, example, table, figure, or claim), a method of preparing a vaccine thin film as described herein (including in an aspect, embodiment, example, table, figure, or claim)

and a method of removing a solvent from a vaccine thin film as described herein (including in an aspect, embodiment, example, table, figure, or claim).

In embodiments, to form a powder vaccine, an aqueous vaccine composition is first frozen to form a frozen vaccine composition, then the frozen water is removed to form the vaccine powder. A fast freezing process is used to form the frozen vaccine composition. A fast freezing process, as used herein, is a process that can freeze a thin film of liquid (less than about 500 microns) in a time of less than or equal to one second. Examples of fast freezing processes that may be used include thin film freezing (TFF), spray freeze-drying (SFD), or spray freezing into liquids (SFL). In the TFF process liquid droplets fall from a given height and impact, spread, and freeze on a cooled solid substrate. Typically, the substrate is a metal drum that is cooled to below 250° K, or below 200° K or below 150° K. On impact the droplets that are deformed into thin films freeze in a time of between about 70 ms and 1000 ms. The frozen thin films may be removed from the substrate by a stainless steel blade mounted along the rotating drum surface. The frozen thin films are collected in liquid nitrogen to maintain in the frozen state. Further details regarding thin film freezing processes may be found in the paper to Engstrom et al. "Formation of Stable Submicron Protein Particles by Thin Film Freezing" Pharmaceutical Research, Vol. 25, No. 6, June 2008, 1334-1346, which is incorporated herein by reference.

Water (e.g. frozen water) is removed from the frozen vaccine composition to produce a vaccine powder. Water (e.g. frozen water) may be removed by a lyophilization process or a freeze-drying process. Water may also be removed by an atmospheric freeze-drying process.

The resulting vaccine powder can be readily reconstituted to form a stable dispersion without significant loss of stability or activity. The vaccine powder may be transported and stored in a wide range of temperatures without concern of accidental exposure to freezing conditions. In addition, the vaccine powder may also be stored at room temperature, which will potentially decrease the costs of vaccines. In fact, it is generally less costly to transport dry solid powder than liquid.

Currently human vaccines (e.g. marketed and/or approved human vaccines, such as FDA approved human vaccines) that have aluminum-containing adjuvant are all administered by needle-syringe-based injections. It would be beneficial to patients and the healthcare system if the vaccines were administered non-invasively without hypodermic needles. Our dried aluminum-containing vaccine powder can potentially be administered by an alternative route such as, but not limited to, inhalation as a dried powder, intradermally using a solid jet injection device (e.g., powder jet injector), orally in tablets or capsules, buccally in buccal tablets or films, or vaginally using a special vaginal drug delivery device. The above-mentioned routes of administration are not only more convenient and friendly to patients, but more importantly they can enable the induction of mucosal immune responses. Functional antibodies in the mucosal secretion (e.g., nasal mucus, bronchoalveolar mucus, or the gastrointestinal mucus) of a host can effectively neutralize pathogens or toxins even before they enter the host.

Described herein are compositions and methods for preparing a vaccine thin film or a dry vaccine by spraying or dripping droplets of a liquid vaccine (e.g. aluminum adjuvant containing) such that the antigenic protein adsorbed to the aluminum adjuvant in the liquid vaccine (e.g. aluminum adjuvant containing) is exposed to an vapor-liquid interface of less than 500 cm$^{-1}$ area/volume (e.g. less than 50, 100, 150, 200, 250, 300, 400) and contacting the droplet with a freezing surface having a temperature lower than the freezing temperature of the liquid vaccine (e.g. aluminum adjuvant containing) (e.g. has a temperature differential of at least 30° C. between the droplet and the surface), wherein the surface freezes the droplet into a thin film with a thickness of less than 500 micrometers (e.g. less than 450, 400, 350, 300, 250, 200, 150, 100, or 50 micrometers) and a surface area to volume between 25 to 500 cm$^{-1}$. In embodiments, the method may further include the step of removing the liquid (e.g. solvent, water) from the frozen material to form a dry vaccine (e.g. particles). In embodiments, the droplets freeze upon contact with the surface in less than 50, 75, 100, 125, 150, 175, 200, 250, 500, 1,000 or 2,000 milliseconds. In embodiments, the droplets freeze upon contact with the surface in less than 50 or 150 milliseconds. In embodiments, the droplet has a diameter between 2 and 5 mm at room temperature. In embodiments, the droplet forms a thin film on the freezing surface of between 50 and 500 micrometers in thickness. In embodiments, the droplets have a cooling rate of between 50-250 K/s. In embodiments, the particles of the dry vaccine, after liquid (e.g. solvent or water) removal, have a surface area of at least 10, 15, 25, 50, 75, 100, 125, 150 or 200 m$^2$/gr (e.g. surface area of 10, 15, 25, 50, 75, 100, 125, 150 or 200 m$^2$/gr). Minimizing gas-liquid interface can improve protein stability by limiting the amount of protein that can adsorb to the interface.

In embodiments, the droplets may be delivered to the cold or freezing surface in a variety of manners and configurations. In embodiments, the droplets may be delivered in parallel, in series, at the center, middle or periphery or a platen, platter, plate, roller, conveyor surface. In embodiments, the freezing or cold surface may be a roller, a belt, a solid surface, circular, cylindrical, conical, oval and the like that permit for the droplet to freeze. For a continuous process a belt, platen, plate or roller may be particularly useful. In embodiments, the frozen droplets may form beads, strings, films or lines of frozen liquid vaccine. In embodiments, the effective ingredient is removed from the surface with a scraper, wire, ultrasound or other mechanical separator prior to the lyophilization process. Once the material is removed from the surface of the belt, platen, roller or plate the surface is free to receive additional material.

In embodiments, the surface is cooled by a cryogenic solid, a cryogenic gas, a cryogenic liquid or a heat transfer fluid capable of reaching cryogenic temperatures or temperatures below the freezing point of the liquid vaccine (e.g. at least 30° C. less than the temperature of the droplet). In embodiments, the liquid vaccine further includes one or more excipients selected from sugars, phospholipids, surfactants, polymeric surfactants, vesicles, polymers, including copolymers and homopolymers and biopolymers, dispersion aids, and serum albumin. In embodiments, aggregation of the antigenic protein is less than 3% of the total antigenic protein in the vaccine (e.g. irreversible aggregation). In embodiments, the temperature differential between the droplet and the surface is at least 50° C. In embodiments, the excipients or stabilizers that can be included in the liquid vaccines that are to be frozen as described herein include: cryoprotectants, lyoprotectants, surfactants, fillers, stabilizers, polymers, protease inhibitors, antioxidants and absorption enhancers. Specific nonlimiting examples of excipients that may be included in the vaccines described herein include: sucrose, trehaolose, Span 80, Tween 80, Brij 35, Brij 98, Pluronic, sucroester 7, sucroester 11, sucroester 15, sodium lauryl sulfate, oleic acid, laureth-9, laureth-8, lauric acid, vitamin E TPGS, Gelucire 50/13, Gelucire 53/10, Labrafil, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones and tyloxapol.

In embodiments, the method may further include the step of removing the liquid (e.g. solvent or water) from the frozen liquid vaccine to form a dry vaccine. In embodiments, the solvent further includes at least one or more excipient or stabilizers selected from, e.g., sugars, phospholipids, surfactants, polymeric surfactants, vesicles, polymers, including copolymers and homopolymers and biopolymers, dispersion aids, and serum albumin. In embodiments, the temperature differential between the solvent and the surface is at least 50° C.

In embodiments, the resulting powder can be used without further dispersion into an aqueous medium. In other embodiments, the resulting powder can be redispersed into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals (e.g. humans).

In embodiments, is described a single-step, single-vial method for preparing a vaccine thin film or dry vaccine by reducing the temperature of a vial wherein the vial has a temperature below the freezing temperature of a liquid vaccine (e.g. a temperature differential of at least 30° C. between the liquid vaccine and the vial) and spraying or dripping droplets of a liquid vaccine directly into the vial such that the antigenic protein of the liquid vaccine is exposed to a vapor-liquid interface of less than 500 cm$^{-1}$ area/volume, wherein the surface freezes the droplet into a thin film with a thickness of less than 500 micrometers and a surface area to volume between 25 to 500 cm$^{-1}$. In embodiments, the droplets freeze upon contact with the surface in less than about 50, 75, 100, 125, 150, 175, 200, 250, 500, 1,000 or 2,000 milliseconds (e.g. in about 50, 75, 100, 125, 150, 175, 200, 250, 500, 1,000 or 2,000 milliseconds), and may freeze upon contact with the surface in about 50 or 150 to 500 milliseconds. In embodiments, a droplet has a diameter between 0.1 and 5 mm at room temperature (e.g. a diameter between 2 and 4 mm at room temperature). In embodiments, the droplet forms a thin film on the surface of between 50 and 500 micrometers in thickness. In embodiments, the droplets have a cooling rate of between 50-250 K/s. In embodiments, the vial may be cooled by a cryogenic solid, a cryogenic gas, a cryogenic liquid, a freezing fluid, a freezing gas, a freezing solid, a heat exchanger, or a heat transfer fluid capable of reaching cryogenic temperatures or temperatures below the freezing point of the liquid vaccine. In embodiments, the vial may be rotated as the spraying or droplets are delivered to permit the layering or one or more layers of the liquid vaccine. In embodiments, the vial and the liquid vaccine are pre-sterilized prior to spraying or dripping. In embodiments, the step of spraying or dripping is repeated to overlay one or more thin films on top of each other to fill the vial to any desired level up to totally full.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

A. Preparation of Dry Powder Vaccine.

Liquid vaccine was prepared by adding 10 mL of Alhydrogel® (10 mg/mL aluminum, manufactured by Brenntag, and supplied by InvivoGen, San Diego, Calif.) into a 50-mL tube followed by the addition of 10 mL of an OVA solution (1 mg/mL in 0.9% w/v saline solution), and 200 mg of trehalose (Sigma-Aldrich, St. Louis, Mo.) to obtain a final formulation with 2% (w/v) of trehalose, 1% (w/v) of Alhydrogel®, and 0.5 mg/mL of OVA. The vaccine suspension was converted into a dry powder using previously reported thin-film freeze-drying method (Li et al., 2015; Thakkar et al., 2017, U.S. patent application Ser. No. 14/941,323). The powder was dried using a VirTis AdVantage Bench Top Lyophilizer (The VirTis Company, Inc. Gardiner, N.Y.). Lyophilization was performed over 72 hours at pressures less than 200 mTorr, while the shelf temperature was gradually ramped up from −40° C. to 26° C. After lyophilization, the solid dry powder vaccine was transferred into a sealed container and stored in a desiccator.

B. Physicochemical Characterization

1. Particle Size Analysis

Geometric diameter of the dry powder vaccine was determined by low angle light scattering using a Malvern Spraytec® (Malvern, UK) outfitted with an inhalation cell and without an induction port. The nasal dry powder delivery device filled with the powder was secured to the mouth of the induction port by a molded silicone adapter. The measurement was done at a flow rate of 25 L/min, providing a 2 kPa pressure drop across the device. Data acquisition took place over 4 s and only when laser transmission dropped below 95%.

2. Powder Morphology and Uniformity of Distribution

Scanning electron microscopy (SEM) attached to energy-dispersive spectroscopy (EDS) was applied to understand the structure and morphology of the dry powder vaccine, and to determine the uniformity of distribution of the dry powder vaccine. Hitachi 5-5500 SEM (Hitachi High Technologies America, Inc., Pleasanton, Calif.) equipped with EDS was used at 10 kV accelerating voltage after sputter-coating the specimen with silver for 30 s in vacuum. Images at different magnifications are photographed from SEM, and EDS plots showing elemental mapping are reported.

3. Flow Properties

The tapped density of the dry powder vaccine was measured according to a method adapted from the United States Pharmacopeia (USP)<616> method I. An adaptation was made due to the limited supply of powder for testing, where a 100-mL graduated cylinder was replaced by a 5-mL graduated cylinder. Hausner ratio and Carr's compressibility index were calculated for each formulation based on USP guidelines. Measurements of the static angle of repose of the dry powder vaccine were conducted as per USP <1174>. Approximately 10 mL of powder was measured using a funnel and a flat collection surface.

C. Aerodynamic Assessment of the Dry Powder Vaccine

Aerodynamic assessment of the dry powder vaccine intended for nasal administration was performed in a nasal cast model. This cast model is made from CT scans of human adult noses and can be divided into four sections representing the anterior region making up the vestibule (V) and nasal valve area; lower, middle and upper turbinates collectively called posterior nasal cavity (P); nasopharynx region (N); and the post-nasal fraction (F), which can either be collected in a cup if the model is operated without simulated inspiration airflow, or a filter is connected to the nasopharynx section if operated at a normal nasal breathing of 15 L/min. The cast was coated with 1% Tween 20 in methanol prior to deposition studies to mimic the mucus layer and minimize particle bounce (ScherlieB and Trows, 2011). The formulations were administered to the cast with a newly developed nasal dry powder delivery device. The spray plume angle was set at 30°, and the tip of the device was inserted at a distance of 5 mm. After administration, the cast was disassembled and all parts were washed with 2% nitric acid carefully to collect the deposited fractions. Aluminum content was determined using a Varian 710-ES Inductively Coupled Plasma-Optical Emission Spectrometer (ICP-OES) in the Civil Architectural and Environmental Engineering Department at The University of Texas at Austin. The deposition profile is shown as % deposition of recovery in different sections of the cast model.

D. Animal Studies

All animal studies were conducted following the U.S. National Research Council Guidelines for the Care and Use of Laboratory Animals. The Institutional Animal Care and Use Committee at The University of Texas at Austin approved the animal protocol. Female Sprague-Dowley rats, 6-8 weeks of age, were from Charles River Laboratories Inc. (Wilmington, Mass.). Rats were dosed intranasally on days 0, 14 and 28 with the dry powder vaccine (IN Powder, n=4) using the nasal dry powder delivery device. The rats were anesthetized and placed on their back at an angle of 45°. The exit diffuser of the device loaded with the vaccine powder was placed in the right nostril of the anesthetized rat. The plunger of the syringe that contains 1 mL of air was depressed to create a powder plume of the vaccine in the nasal cavity. As controls, rats were also intranasally dosed with the liquid vaccine (IN Liquid, n=4), saline (n=5), or subcutaneously (s.c.) injected with the liquid vaccine (SC Liquid, n=4). For intranasal dosing of the liquid vaccine and normal saline, rats were placed on their back at an angle of 45° after anesthesia. The liquid vaccine or normal saline was administered using a fine pipette tip into the external nares with 10 μL volume in each nostril. The dose of OVA was 20 μg per rat, and 400 μg for Alhydrogel® in the IN Liquid and SC Liquid groups. In the IN Powder group, the dose of OVA in the first immunization was 21.6+/−3.0 mcg/rat. However, in the second and third immunizations, largely because the amount of dry powder that came out of the nasal dry powder delivery device varies each time, some rats were dosed twice, leading to an increase in the dose of OVA to more than 20 mcg/rat (i.e. 49.4+/−6.6 meg/rat and 85.7+/−19.5 meg/rat, respectively). Four weeks after the third dose, rats were euthanized to collect blood, nasal wash, and bronchoalveolar lavage (BAL). Nasal wash and BAL were collected as previously described using 500 μL of sterile PBS (Lowrie and Whalen, 2000).

The anti-OVA IgG and IgA levels in serum samples, nasal washes, and BAL samples were determined using enzyme-linked immunosorbent assay (ELISA) (Sloat et al., 2010). Briefly, EIA/RIA flat bottom, NUNC Maxisorp, 96-well plates (Thermo Fisher) were coated with 1 ng/μL of OVA solution in carbonate buffer (0.1 M, pH 9.0) overnight at 4° C. Plates were blocked with horse serum for one hour before adding the blood serum. Horse radish peroxidase (HRP)-labeled goat anti-mouse immunoglobulin (IgG or IgA, 5000-fold dilution, Southern Biotechnology Inc., Birmingham, Ala.) was added into the plates, and the presence of bound antibody was detected in the presence of 3,3',5,5'-tetramethylbenzidine solution (TMB, Sigma-Aldrich). The absorbance was read at 450 nm.

Brain tissues were collected from the rats upon euthanasia. The tissues were weighed, desiccated at 60° C. for 12 h, and then incinerated with nitric acid (6.6 N) at 60° C. for 15 h. Aluminum content was determined using an Agilent 7500ce quadruple Inductively Coupled Plasma attached with Mass Spectrometer (ICP-MS) in the Department of Geological Sciences at The University of Texas at Austin. ICP-MS has a detection limit of 1 ng/L (parts per trillion) for aluminum (Thermo Elemental, 2001). The aluminum levels are normalized to the dry weight of the brain tissues.

Noses of rats immunized by the intranasal (dry powder and liquid vaccine) and subcutaneous routes were prepared for histological examination. For this, the noses were separated, immobilized and decalcified. Afterwards the samples were sliced horizontally from the nostrils to the nasopharynx and slices were stained with hematoxylin and eosin (H&E) stain for histological evaluation. Microscopy images of the nasal cross section and close ups of the epithelium have been taken.

E. Statistics

Statistical analyses were completed by performing two-tailed Student's t-test for two-group analysis or one-way ANOVA followed by Tukey's post hoc analysis for multiple group comparisons (GraphPad Prism 7 software, La Jolla, Calif.). A p value of <0.05 (two-tail) was considered significant.

Example 2—Physicochemical Properties of the Dry Powder Vaccine

F. Flow Properties of the Dry Powder Vaccine

The flow properties measure the cohesive forces of a powder. In this study, the dry powder vaccine was prepared to explore the feasibility of intranasal administration, not their flow properties per se. However, the flow properties do affect the performance of the final product (Martin et al., 1993). Also, because nasal delivery requires a fluidization of the powder bed, it is conceivable that the flow properties of the dry powder vaccine could affect the emitted dose from the nasal delivery device and the deposition of the vaccine in the nasal cavity.

The bulk and tapped densities of the dry powder was 0.040±0.003 and 0.051±0.007 g/mL, respectively (Table 1). The Hausner ratio and Carr's compressibility index of the dry powder vaccine was calculated to be 1.28±0.07 and 21.80±4.25%, respectively, indicating that the flow property of the powder is 'passable'. The angle of repose of the dry powder was 25.94±6.30°, which indicates a good flow property. The discrepancy in the flow property between the two methods of measurement could be explained by the porous and brittle nature of the thin-film freeze-dried vaccine powder, making it more compressible.

G. Powder Morphology and Uniformity of Distribution

According to USP chapter <905>, each unit in a batch should have a drug substance content within a narrow range of the claimed limit, which is referred to as uniformity of the dosage unit. The International Council for Harmonization of Technical Requirements for Pharmaceuticals for Human Use (ICH) Q6B also provides specifications for biotechnological and biological products to perform uniformity test of the dosage units of the biologicals. SEM/EDS has an X-ray spectrometer attached to SEM, which allows elemental analysis in addition to SEM. SEM/EDS could be employed to determine the qualitative distribution of the dry powder vaccine by taking advantage of the elemental aluminum in the formulation. This analysis gives an indication of how the vaccine is distributed in the dry powder form. Three random areas in an SEM graph (FIG. 1A, upper panel of FIG. 1B) were chosen for analysis, and four elements, Al, O, Na and Cl, were analyzed. SEM/EDS showed the presence of all four elements analyzed (FIG. 1B-C). The spectrum analysis and EDS map indicate a homogeneous distribution of the elements, implying that the vaccine was uniformly distributed in the thin-film freeze-dried powder.

H. Intranasal Dry Powder Delivery Device and Powder Characterization

A new nasal dry powder delivery device was developed for this study. The device includes a housing reservoir (e.g. the hub of an oral feeding/gavage needle) and a pressurizing mechanism operable to pressurize gas/air chamber (e.g. similar to a syringe) to desired pressure. The dry powder vaccine is loaded into the housing reservoir. Depressing the syringe plunger pushes air through the device, creating a powder plume that exits the orifice of the device (FIG. 2A). The particle size of the dry powder vaccine was measured using a Malvern's Spraytec instrument and shown in FIG. 2B. The median diameter of the vaccine dry powder was 12.55±4.69 µm. According to FDA, particles greater than 10 µm are expected to deposit in the nasal cavities after nasal administration (FDA, 2002).

I. Aerodynamic Assessment of Dry Powder Vaccine

The nose or nasal cavity are the most easily accessible part of the respiratory system. It is worth noting that release of antigen from the powder vaccine to the nasal cavity must take into account several factors, including wettability, dissolution rate, and the interaction of antigen-adjuvant with the mucus. However, for a nasal vaccine to afford protection, vaccines must present antigen to the target lymphoid tissues in the nose. Nose-associated lymphoid tissue (NALT) in rodents refers to a pair of aggregated lymphoid tissues in the bottom of nasal ducts. In human nose cavity, the Walderyer's ring, a well-known group of tonsils that include the adenoid, tubal, palatine, and lingual tonsils, is the key lymphoid tissue, however (Hellings et al., 2000). A post mortem study by Debertin and colleagues provided the first evidence of the existence of NALT, in addition to the Walderyer's ring, in young children (Debertin et al., 2003). This study in young children found disseminated aggregates of lymphoid tissues in 38% of the cases, mainly in the superior nasal meatus (30.1%), the middle concha (26.4%), the inferior nasal concha (13.5%), and the superior nasal concha (10.4%). Pabst stated that there is not any reported data on the frequency of NALT in adolescents and adults (Pabst, 2015).

Evaluation of nasal deposition of the dry powder vaccine would be a good quality control check in the formulation development of nasal vaccines because of the fact that there are no guidelines or international consensus regarding the relationship between aerosol characteristics and deposition sites within the nasal cavities (Le Guellec et al., 2014). Nasal casts obtained from the CT scans of five adult humans were used to predict the deposition of the dry powder vaccine after nasal administration. FIG. 3A shows the representative image of the different sections of the nasal casts used. The deposition study was carried out at a 15 L/min. According to FIG. 3B, 62.20±8.14% the vaccine dry powder was recovered from the casts. Out of the recovered powder, 64% was in the posterior nasal cavity. Overall, the nasal deposition can be deemed good, considering out of the total powder recovered (62.20±8.14%), about 90% of the stayed in the nose, and only around 10% of the powder going to post nasal fraction.

Example 3—In Vivo Testing of the Dry Powder Vaccine

J. Immunogenicity of the Dry Powder Vaccine after Intranasal Administration

To evaluate the feasibility of administering the dry powder vaccine directly to the nose (IN Powder) to induce immune response, rats were nasally administered with the dry powder vaccine using the nasal dry powder delivery device. The immune responses induced by the same liquid vaccine after intranasal (IN Liquid) or subcutaneous (SC Liquid) administration were also assessed. Shown in FIG. 4 are the OVA-specific antibody levels induced, i.e. serum IgG titers and mucosal IgA titers in nasal wash and BAL. Intranasal administration of the dry powder vaccine induced OVA-specific IgG response in rat serum samples to a level that is comparable to that induced by intranasal or subcutaneous administration of the same OVA-Alhydrogel® vaccine in a liquid dispersion (FIG. 4A). Importantly, intranasal administration of the dry powder vaccine also induced significantly higher OVA-specific IgA in rat nasal wash and BAL samples, as compared to subcutaneous injection of the same OVA-Alhydrogel® vaccine in a liquid dispersion (FIG. 4B-C). H&E staining of mouse nasal cavities did not reveal any difference among rats that received the dry powder intranasally, the liquid vaccine intranasally or subcutaneously, or normal saline intranasally (FIG. 5), indicating that the dry powder vaccine was well tolerated locally when given intranasally.

K. Aluminum Biodistribution in Brain

Aluminum containing adjuvants possess excellent safety profile of close to a century (Thakkar and Cui, 2017; Gupta et al., 1993; O'Hagan, 2000), and it was suggested that all the injected aluminum hydroxide may be dissolved and absorbed eventually (Flarend et al., 1997; Hem, 2002). Due to the large size of the particulates in the vaccine dry powder and the liquid vaccine (i.e. ×50 of ~12 µm and 8 µm, respectively), the particles are expected to largely stay in the nasal cavity after nasal administration (Hatch, 1961; Stuart; 1973). However, there is a potential of brain exposure of aluminum via the olfactory epithelium (Djupesland et al., 2013; Pauluhn, 2009; Perl and Good; 1987). In one study, no significant brain aluminum levels were seen in rats after 4 weeks of continuous exposure of insoluble aluminum (oxy) hydroxide (Pauluhn, 2009), while others showed elevated brain levels in rabbits after one month of continuous nasal exposure of soluble aluminum in solutions (e.g. aluminum lactate or aluminum chloride, as 'Gelfoam') (Perl and Good; 1987).

Aluminum levels in the brain tissues of the immunized rats were measured after terminal euthanasia (i.e. four weeks after the last immunization). FIG. 6 shows the levels of aluminum determined in rat brain tissues. There was not any significant difference in aluminum levels among all four groups. This indicates that intranasal administration of the vaccine, in liquid or dry powder form, will not likely lead to a higher level of aluminum in the brain than subcutaneous injection of the same liquid vaccine. For rodents, about 50% of the nasal cavity is lined with olfactory epithelium, compared to 3% for humans (Harkema et al., 2006), which will likely further limit nose to brain transport in humans, if any. Therefore, it is very unlikely that transient nasal exposure of the insoluble aluminum salt in vaccines for 1-3 times at a relatively low dose would result in an elevated level of aluminum in brain.

These results indicate that the aluminum salts in existing injectable human vaccines may be used as nasal mucosal vaccine adjuvants. Furthermore, administering aluminum salt-adjuvanted vaccine powder intranasally can potentially address the cold-chain requirement associated with aluminum salt-adjuvanted liquid vaccines as well as the limitations associated with hypodermic needle-based injections. These results also demonstrate the feasibility of intranasally administering aluminum salt-adjuvanted dry powder vaccines to induce specific mucosal and systemic responses in a rat model. New and existing aluminum salt-containing vaccines may be converted into dry powder using the thin-film freeze-drying technology and administered without the need for needles using a nasal dry powder delivery device.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Butler et al., *J Immunol.*, 104(6):1396-400, 1970.
Chen et al., *J Control. Rel.*, 152: 412-822, 2011.
Davis S S, *Adv Drug Deliv Rev.*, 51(1-3):21-42, 2001.
Debertin et al., *Clinical & Experimental Immunology.*, 134(3):503-7, 2003.
Djupesland et al., *J Cereb Blood Flow Metab.*, 33(5):793-4, 2013.
Eisenbarth et al., *Nature*, 453: 1122-1126, 2008.
Engstrom et al., *Pharmaceutical research*, 25: 1334-1346, 2008.
FDA Guidance for Industry, *Nasal Spray and Inhalation Solution, Suspension, and Spray Drug Products—Chemistry, Manufacturing, and Controls Documentation*, 2002.
Flarend R E et al., *Vaccine*, 15(12-13):1314-8, 1997.
Franchi et al., *Eur J Immunol*, 38:2085-2089, 2008.
Glenny et al., *J Pathol. Bacteriol*, 34: 267-275, 1931.
Gupta et al., *Vaccine*, 11(3):293-306, 1993.
Harkema et al., *Toxicologic Pathology*, 34(3):252-69, 2006.
Hashigucci et al., *Vaccine.* 14(2):113-9, 1996.
Hatch T F., *Bacteriol Rev.* 25:237-40, 1961.
Hellings et al., *Acta Otorhinolaryngol Belg.*, 54(3):237-41, 2000.
Hem S L., *Vaccine*, 20 Suppl 3:S40-3, 2002.
Hem and Hogenesch, *Expert review of vaccines*, 6: 685-698, 2007.
Hogenesch H., *Vaccine*, 20: S34-39, 2002.
Homung et al., *Nat Immunol*, 9:847-856, 2008.
Huang et al., *Vaccine*, 23(6):794-801, 2004.
Isaka et al., *Vaccine*, 16(17):1620-6, 1998.
Isaka et al., *Nagoya medical journal*, 45(1):5-15 2001.
Jones et al., *The Journal of biological chemistry*, 280: 13406-13414, 2005.
Kool et al., *Journal of immunology*, 181:3755-3759, 2008.
Lawson L B et al., *Curr Opin Immunol.*, 23(3):414-20, 2011.
Le Guellec et al., *Pharm Res.*, 31(1):228-37, 2014.
Li et al., *Journal of Controlled Release*, 204:38-50, 2015.
Lieberman, *Pharmaceutical Dosage Forms*, vols. 1-3, 1992.
Lloyd, *The Art, Science and Technology of Pharmaceutical Compounding*, 1999. Lowrie and Whalen, *DNA vaccines: methods and protocols: Springer Science & Business Media*, 2000.
Mannhalter et al., *Clinical and experimental immunology*, 61: 143-151, 1985.
Martin et al., *Physical pharmacy: physical chemical principles in the pharmaceutical sciences.* 1993.
Mestecky et al., *J Controlled Release*, 48(2):243-57, 1997.
Milstien et al., *World Health Organization.* 2006.
O'Hagan D T. *Vaccine Adjuvants: Preparation methods and Research protocols*, 2000.
O'Hagan et al., *Biomol Eng.*, 18:69-85, 2001.
Pabst R., *Vaccine*, 33(36):4406-13, 2015.
Pauluhn J., *Toxicol Sci.*, 109(1):152-67, 2009.
Perl and Good, *Lancet*, 1(8540):1028, 1987.
Pickar, *Dosage Calculations*, 1999.
Remington, *The Science and Practice of Pharmacy*, 20th Edition, 2003.
Romero Mendez et al., *Vaccine*, 25: 825-833, 2007.
Scherließ and Trows, *Procedia in Vaccinology*, 4:113-9, 2011.
Singh and O'Hagan, *Nat Biotechnol.* 17:1075-81, 1999.
Sloat et al., *Journal of controlled release: official journal of the Controlled Release Society*, 141(1):93-100, 2010.
Smith et al., *Vaccine*, 21(21-22):2805-12, 2003.
Stuart B O. *Arch Intern Med.*, 131(1):60-73, 1973.
Thakkar et al., *Hum Vaccin Immunother.*, 13(4):936-46, 2017.
Thakkar and Cui, *Vaccine Adjuvants: Methods and Protocols. Methods in Molecular Biology*, p. 181-99, 2017.
Thermo Elemental, AAS, GFAAS, ICP or ICP-MS? Which technique should I use. An elementary overview of elemental analysis, 2001.
Tritto et al., *Vaccine*, 27:3331-3334, 2009.
Ulanova et al., *Infection and immunity*, 69: 1151-1159, 2001.
U.S. patent application Ser. No. 14/941,323
Xu et al., *Human Vaccines and Immunotherapeutics*, 2017.

What is claimed is:

1. A method for stimulating a systemic immune response in a patient, comprising intranasally administering to the patient an aerosol dry powder cloud composition from an applicator or inhaler comprising an antigenic polypeptide adsorbed to an aluminum adjuvant, wherein the aerosol dry power cloud composition is composed of particles of average 5-15 μm in diameter.

2. The method of claim 1, wherein at least 75% of said antigenic polypeptide is adsorbed to said aluminum adjuvant.

3. The method of claim 1, wherein said aluminum adjuvant is aluminum (oxy)hydroxide, aluminum (hydroxyl) phosphate or potassium aluminum sulfate.

4. The method of claim 1, the composition comprising less than 2% water.

5. The method of claim 1, wherein at least 80%, 85% or 90% of said antigenic protein is adsorbed to said aluminum adjuvant.

6. The method of claim 1, further comprising an excipient, selected from a salt, sugar, buffer, detergent, polymer, amino acid, or preservative.

7. The method of claim 6, wherein said excipient is disodium edetate, sodium chloride, sodium citrate, sodium succinate, sodium hydroxide, sodium glucoheptonate, sodium acetyltryptophanate, sodium bicarbonate, sodium caprylate, sodium pertechnetate, sodium acetate, sodium dodecyl sulfate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol, glyclyglycine, thimerosal, parabens, gelatin, Formaldehyde, Dulbecco's modified eagles medium, hydrocortisone, neomycin, Von Willebrand factor, gluteraldehyde, benzethonium chloride, white petroleum, p-aminopheyl-p-anisate, monosodium glutamate, beta-propiolactone, acetate, citrate, glutamate, glycinate, Lactate, Maleate, phosphate, succinate, tartrate, tris, carbomer 1342 (copolymer of acrylic acid and a long chain alkyl methacrylate cross-linked with allyl ethers of pentaerythritol), glucose star polymer, silicone polymer, polydimethylsiloxane, polyethylene glycol, polyvinylpyrrolidone, carboxymethylcellulose, poly(glycolic acid), poly(lactic-co-glycolic acid), polylactic acid, dextran 40, or poloxamer.

8. The method of claim 6, wherein the aerosol dry powder cloud composition comprises about 50% to 99% wt/wt of said excipient.

9. The method of claim 1, wherein the antigenic polypeptide is from an infectious agent.

10. The method of claim 1, wherein the antigen is from *Clostridium tetani, Streptococcus pneumonia*, Hepatitis A, Hepatitis B, *Haemophilus* influenza, *Corynebacterium diphtheria, Bordetella pertussis*, Human papillomavirus, Bacillus anthracis, Rabies virus, Japanese encephalitis virus, or Poliovirus.

11. A nasal spray comprising a device comprising dry powder composition comprises an antigenic polypeptide adsorbed to an aluminum adjuvant; and an applicator capable of dispersing an aerosol cloud of the dry powder composition into the nasal cavity, or a kit comprising the same.

* * * * *